(12) United States Patent
Leinonen et al.

(10) Patent No.: US 10,537,240 B2
(45) Date of Patent: Jan. 21, 2020

(54) METHOD FOR ASSESSING FUNCTION OF THE VISUAL SYSTEM AND APPARATUS THEREOF

(71) Applicant: Ocuspecto Oy, Turku (FI)

(72) Inventors: Markku Leinonen, Turku (FI); Tapio Mantysalo, Hevonpaa (FI)

(73) Assignee: Ocuspecto Oy, Turku (FI)

( * ) Notice: Subject to any disclaimer, the term of this patent is extended or adjusted under 35 U.S.C. 154(b) by 119 days.

(21) Appl. No.: 15/258,948

(22) Filed: Sep. 7, 2016

(65) Prior Publication Data

US 2017/0042418 A1   Feb. 16, 2017

Related U.S. Application Data

(63) Continuation of application No. 14/373,027, filed as application No. PCT/FI2013/050266 on Mar. 11, 2013, now Pat. No. 9,456,740.

(Continued)

(30) Foreign Application Priority Data

Mar. 9, 2012   (FI) ...................................... 20125256

(51) Int. Cl.
  *A61B 3/024*   (2006.01)
  *A61B 5/11*    (2006.01)
  (Continued)

(52) U.S. Cl.
  CPC .............. *A61B 3/024* (2013.01); *A61B 3/005* (2013.01); *A61B 3/0008* (2013.01);
  (Continued)

(58) Field of Classification Search
  CPC ..... A61B 3/024; A61B 3/0025; A61B 3/0091; A61B 5/16; A61B 3/005; A61B 3/0008;
  (Continued)

(56) References Cited

U.S. PATENT DOCUMENTS 5,035,500 A    7/1991   Rorabaugh et al.
5,422,690 A    6/1995   Rothberg et al.
         (Continued)

FOREIGN PATENT DOCUMENTS

CN   102456317   *   5/2012
JP   2010-526623      8/2010
         (Continued)

OTHER PUBLICATIONS

Carroll et al. "Visual Field Testing: From One Medical Student to Another" http://eyerounds.org/totorials/VF-testing/, 2013.*

(Continued)

*Primary Examiner* — George G King
(74) *Attorney, Agent, or Firm* — James C. Lydon

(57) ABSTRACT

This invention relates to a method for providing markers for evaluating and/or practising the visual field recognizable by an eye, and/or eyes, and/or visual system of a person. The method relies on the reporting of the person of identifications of fixation objects only identifiable when the eye or eyes of the person are accurately fixated on the fixation object. Accordingly active monitoring of a saccade, if a saccade triggering stimulus is employed; or smooth pursuit, if smooth pursuit triggering stimulus is employed, of the eye of the person is not needed for determining whereto to eye or eyes are fixated. The present invention also relates to the use of a system employing the method of the invention. The present invention further relates to a system for the method of the invention and a software product for the system.

4 Claims, 12 Drawing Sheets

Related U.S. Application Data

(60) Provisional application No. 61/608,773, filed on Mar. 9, 2012.

(51) Int. Cl.
*A61B 3/00* (2006.01)
*A61B 3/02* (2006.01)
*A61B 5/00* (2006.01)

(52) U.S. Cl.
CPC .......... *A61B 3/0025* (2013.01); *A61B 3/0058* (2013.01); *A61B 3/0091* (2013.01); *A61B 3/022* (2013.01); *A61B 5/1114* (2013.01); *A61B 5/6814* (2013.01)

(58) Field of Classification Search
CPC ..... A61B 3/0058; A61B 3/022; A61B 5/1114; A61B 5/6814
USPC ....................................................... 351/224
See application file for complete search history.

(56) References Cited

U.S. PATENT DOCUMENTS

| | | |
|---|---|---|
| 5,565,949 A | 10/1996 | Kasha, Jr. |
| 5,880,812 A | 3/1999 | Solomon |
| 5,920,375 A | 7/1999 | Fahle et al. |
| 2005/0128434 A1 | 6/2005 | Ianchulev et al. |
| 2006/0087618 A1 | 4/2006 | Smart et al. |
| 2006/0114414 A1 | 6/2006 | McGrath et al. |
| 2006/0232742 A1 | 10/2006 | Nakamura et al. |
| 2007/0066916 A1* | 3/2007 | Lemos ................. A61B 3/113 600/558 |
| 2007/0182928 A1 | 8/2007 | Sabel |
| 2008/0186707 A1* | 8/2008 | Ku ......................... G09G 3/20 362/253 |
| 2008/0212032 A1 | 9/2008 | Seiller et al. |
| 2010/0128222 A1 | 5/2010 | Donaldson et al. |
| 2010/0195051 A1 | 8/2010 | Murray et al. |
| 2013/0128229 A1* | 5/2013 | Huang .................... G06K 9/46 351/239 |

FOREIGN PATENT DOCUMENTS

| | | |
|---|---|---|
| JP | 2011-161122 | 8/2011 |
| WO | 2005093679 | 10/2005 |
| WO | 2008005848 | 1/2008 |
| WO | 2008078106 | 7/2008 |

OTHER PUBLICATIONS

Partial Translation of Office Action in Japanese Application 2014-560420.

* cited by examiner

METHOD FOR ASSESSING FUNCTION OF THE VISUAL SYSTEM AND APPARATUS THEREOF

FIELD OF THE INVENTION

This invention relates to methods and apparatus for assessing and practicing function of the visual system, especially visual field, visual search ability, visual decision making, saccadic eye movement and smooth pursuit of the eye. More specifically this invention relates to method of accurately determining the orientation of the eye or eyes. With this invention it is possible to verify without active monitoring of the eye or eyes that the visual axis or the fovea centralis of the retina of the eye or eyes is aimed at, or fixates to a given fixation object at a defined time point by designing the features of the fixation object to be detectable only by foveal vision.

BACKGROUND OF THE INVENTION

The publications and other materials used herein to illuminate the background of the invention, and in particular, cases to provide additional details respecting the practice, are incorporated by reference.

In existing devices and methods for assessing the visual field of the eye there are several problems which affects the reliability of the results or makes the testing situation difficult for the person to be tested. In visual field testing it is essential that the orientation of the eye, i.e. where the line of sight (visual axis) or the fovea centralis of the retina of the eye is aimed at, or fixates, is accurately known. Only after this precise information one can present a stimulus in an accurate location in the visual field of a person.

In existing devices and methods the subject is asked to concentrate on a given, static fixation point and report on the presence and position of stimuli presented to their peripheral vision. This prolonged attempt of fixation on a given point is very unnatural and often uncomfortable eye behaviour for a person. Additionally the ability of the subject to accurately fixate is known to be poor especially over an extended period and so the accuracy of the visual field measurement is compromised.

In existing devices and methods the monitoring of the accuracy of the fixation of the eye is usually done with the help of an optical telescope which is focused to the pupil of the eye to be examined. The crosshair of the telescope is centred to the pupil and all stimuli which are presented when the pupil is not in the middle of the crosshair are discarded. This monitoring of the fixation of the eye can be done visually by the examiner, which is rather unreliable and depends on the alertness of the examiner, or with electronic camera image processing system, or with automatic electronic video camera based eye-tracker, which requires complex and therefore expensive electronic systems and also requires prior calibration procedure.

The existing devices for examination of the visual field are usually large and technically complex, and therefore expensive, requiring a separate instrument table which occupies plenty of floor space in small examination rooms when not in use.

In some existing devices and methods for assessing ocular motor functions the orientation of the eye, i.e. where the line of sight (visual axis) or the fovea centralis of the retina of the eye is aimed at, or fixates, is monitored usually by automatic electronic video based eye-tracker, which requires complex and therefore expensive electronic systems. Before this kind of device can provide accurate information about the orientation of the eye, a calibration procedure must be conducted so that the device can match a detected specific position of the eye to eye's foveal fixation to known fixation target.

OBJECT AND SUMMARY OF THE INVENTION

Another object of the present invention is to provide use of a system for providing markers for evaluating and/or practicing the visual field recognizable by an eye, and/or eyes, and/or visual system of a person.

A still further object of the present invention is to provide a software product for a system for carrying out a method for providing markers for evaluating, and/or practicing the visual field recognizable by the eye, and/or eyes, and/or visual system of a person.

The present invention provides a method for providing markers for evaluating and/or practicing the visual field recognizable by an eye, and/or eyes, and/or visual system of a person.

A still further object of the present invention is to provide a software product for a system for carrying out a method for providing markers for evaluating, and/or practicing the visual field recognizable by the eye, and/or eyes, and/or visual system of a person.

The present invention provides a method for providing markers for evaluating and/or practising the visual field recognizable by an eye, and/or eyes, and/or visual system of a person wherein said method comprises evaluating
- the ability of the peripheral visual field to detect a saccade triggering stimulus STS at a specific location of the visual field of said eye or eyes of said person,
- the ability of the eye or eyes of a person to accurately hit a target by executing a saccade triggered by a saccade triggering stimulus STS at a specific location of the visual field of said eye or eyes of said person, and/or
- the accuracy of smooth pursuit of the eye or eyes of a person, said smooth pursuit being triggered by a smooth pursuit triggering stimulus SPTS;

by
a) having said eye or eyes, fixated on a preceding fixation object $FO_p$, which $FO_p$ is identifiable by the person only when said eye or eyes is accurately fixated on said $FO_p$, i.e. when said $FO_p$ is positioned at the fovea of said eye or eyes of said person, execute a saccade or smoothly pursue in response to provided said STS or said SPTS, respectively, b) providing a fixation object FO which FO is identifiable by the person only when said eye or eyes is accurately fixated on said FO, i.e. when said FO is positioned at the fovea of said eye or eyes of said person, at a location whereto said eye or eyes of said person is expected to be fixated at the end of said saccade or during said smooth pursuit, c) having said person identify said FO, said identification referred to as an identification of said FO, d) having said person report said identification of said FO, e) recording correctness of reported identification of said FO and time points of
  providing said STS and/or FO, if said SPTS is employed, and
  reporting of identification of said FO, f) calculating time period between providing said STS or FO, and reporting of said identification of FO, if said STS is employed; and/or time period between providing said FO and reporting of said identification of FO, if said SPTS is employed;

wherein an incorrect or missing reporting of identification, and/or extended delay in a correct reporting of identification, compared to delay regarded normal for persons corresponding to said person, or compared to delays for other locations of the visual field of said eye or eyes of said person, or compared to delays of said person obtained at earlier time point in his or her life, are markers for an abnormal and/or deteriorated ability of said eye or eyes of said person to detect said STS at said specific location of the visual field of said eye or eyes of said person, ability of said eye or eyes of said person to accurately hit a target by executing a saccade triggered by said STS, ability of said person to identify said FO, accuracy of smooth pursuit of said eye or eyes of said person, said smooth pursuit being triggered by said SPTS, and/or function of said visual system of said person.

The present invention also provides a use of a system for providing markers for evaluating and/or practicing the visual field recognizable by an eye, and/or eyes, and/or visual system of a person, which system comprises a) a display or displays capable of providing at least a saccade triggering stimulus STS or a smooth pursuit triggering stimulus SPTS, and a fixation object FO at specified locations;

b) a reporting means with which a person identifying said FO can report to said data processing unit his or her identification of said FO;

c) a data processing unit with software for at least i) providing, on said display or displays, at least said STS and/or SPTS, and said FO at said specified locations;

ii) recording correctness of reported identification of said FO;

iii) recording time points of providing said STS and/or SPTS, and a FO at said specified locations; and reporting of said identification; and iv) calculating at least time period between providing said STS or FO, and said reporting of identification of FO, if said STS is employed; and/or time period between providing said FO and said reporting of identification of FO, if said SPTS is employed;

wherein said STS and/or SPTS, and fixation objects FOs are provided on said display or displays, time points and reporting of identification are registered; and time periods calculated according to methods of the present invention.

The present invention further provides a system for providing markers for evaluating and/or practicing the visual field recognizable by an eye, and/or eyes, and/or visual system of a person by carrying out any of the methods of the present invention, which system comprises a) a display or displays capable of providing at least a saccade triggering stimulus STS or a smooth pursuit triggering stimulus SPTS, and a fixation object FO at specified locations;

b) a reporting means with which a person identifying said FO can report to said data processing unit his or her identification of said FO;

c) a data processing unit with software for at least i) providing, on said display or displays, at least said STS and/or SPTS, and said FO at said specified locations;

ii) recording correctness of reporting of identification of said FO;

iii) recording time points of providing said STS and/or SPTS, and said FO at said specified locations; and reporting of said identification; and iv) calculating at least time period between providing said STS and reporting of said identification of FO, if said STS is employed; and/or time period between providing said FO and reporting of said identification of FO, if said SPTS is employed;

wherein d) said software of said data processing unit carries out evaluation of the visual field recognizable by the eye or eyes and/or oculomotor functions of said person according to any of the methods of the present invention.

The present invention still further provides a software product for a system for carrying out any of the methods for providing markers for evaluating, and/or practicing the visual field recognizable by the eye, and/or eyes, and/or visual system of a person according to any of the present invention, wherein said software product comprises means for at least i) providing, on a display or displays, at least a saccade triggering stimulus STS and/or smooth pursuit triggering stimulus SPTS, and a fixation object FO at specified locations;

ii) recording correctness of reported identification of FO by said eye or eyes of said person;

iii) recording time points of providing said STS and/or SPTS, and said FO at said specified locations; and reporting of said identification; and iv) calculating at least time period between providing said STS or FO, and reporting of said identification of FO; and/or time period between providing said FO and reporting of said identification of FO, if said SPTS is employed.

DETAILED DESCRIPTION OF THE INVENTION

Figure 1:
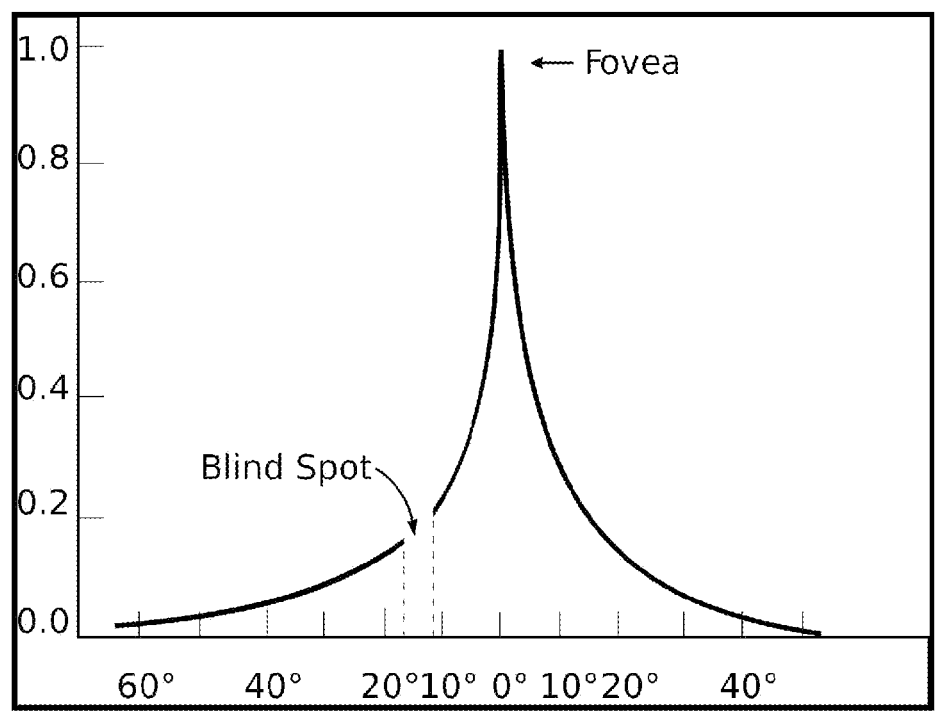
FIG. 1 illustrates the visual acuity of the eye along the horizontal meridian of the visual field. Visual acuity at the fovea centralis of the retina is good and drops abruptly peripherally.

This invention relates to methods and apparatus for assessing function of the visual system. This invention is useful inter alia in the diagnosis of glaucoma and other visual disorders which affect the visual field of the eye, in Alzheimer disease and other brain disorders which affect ocular motor functions or neural connections or functions of various brain areas responsible for visual search and visual decision making, in assessing a person's fatigue, wakefulness and alertness and in assessment of visual fitness for driving a power-driven vehicle or operating machinery. This invention can be used also to assess and practice visual search ability, visual decision making, saccadic eye movements and smooth pursuit of the eye The object of the present invention is to substantially reduce or eliminate the disadvantages mentioned above. In particular the invention makes it possible to know with certainty that the visual axis or the fovea centralis of the retina of the eye is aimed at, or fixates to a given fixation object (FO) at a defined time point. Along with this information it is possible to provide a stimulus to an accurate location of peripheral vision in relation of this location which is the centre of the visual field of a person.

The gist of the invention is in that the person himself reports, by correct identification of a fixation object (FO), whereto the eye of the person has been fixated at any time point of identification. This is accomplished by choosing identification objects identifiable only when the eye is accurately fixated at the fixation object (FO), i.e. the fovea centralis of the retina of the eye is aimed at the fixation object. When fixations to fixation objects (FOs) are reported throughout the examination at different time points of different (or same) fixation objects no need for external monitoring of e.g. saccade or smooth pursuit or fixation of the eye is needed. Accordingly means for external monitoring involving complicated and costly devices and awkward in use, are redundant when employing the present invention.

With the help of the time points of the fixations to fixation objects (FOs) and by designing the paradigm of the test and the characteristics of the stimuli which is used, it is possible to get information about various aspects of the functions of the visual system and the motor response by which the person is reporting the identification of the fixation objects (FOs). E.g. in the case of visual field examinations, similar stimuli can be presented at different locations of the visual field. If the reaction times calculated using the time points of the fixations are longer in some restricted area of the visual field, that could indicate defective vision in that area.

Another alternative could be to compare reaction times calculated using the time points of the fixations, to reaction times regarded normal or to reaction times of the same person obtained earlier in his or her life. In this way one could detect an effect of a brain disease, fatigue or use of alcohol or drugs to the reaction times.

The present invention uses anatomy of the human eye and visual psychophysics for monitoring the fixation of the eye. In the human eye the term fovea (or fovea centralis) denotes the pit in the retina. Foveal vision has many special features which are unique in the visual field of a man. It allows for maximum acuity of vision (FIG. 1). In daylight conditions (i.e. not in dim light) the fovea is also the most sensitive area of visual field for detecting light differences between visual target and the background (differential light sensitivity). Also colour vision is most sensitive in foveal vision.

In the invention the fixation object (FO) for a person to fixate at is designed so that it uses these special features of foveal vision and is recognizable only if the fovea is aimed at the object. Thus, the FO can contain a small character, symbol or pattern which a person must identify and report. Alternatively the FO can be so dim or it can have so faint colour tint that it is only detectable with foveal vision. After having identified the FO the person reports it for example pressing a correct button. At this time point, after correct identification of the FO, the orientation of the eye is accurately known: the fovea is fixating to the FO.

This time point offers a possibility to provide a further stimulus or stimuli at precisely known peripheral locations of the visual field. If a person can detect this new peripheral stimulus, he can, according to the invention, make a rapid eye movement to shift his or her line of sight or redirect the fovea from fixation object FO and make a saccade to this peripheral saccade triggering stimulus (STS). Alternatively so called anti-saccade task paradigm can also be used: the person is instructed to make a saccade to the opposite direction of the STS. A second fixation object ($FO_2$), which has the same design properties as the first fixation object ($FO_1$) and thus is only recognizable by foveal vision can be provided at this symmetrical location of the STS in relation to $FO_1$ or origin of the visual field.

It is possible for the person who has correctly reported the identification of FO by pressing a correct button, to shift his or her gaze direction so that the fovea of the eye is no longer aimed at the FO at the time point when the button is pressed. This can be prevented by replacing the FO at the same location by a feedback stimulus (FBS), which gives visible feedback about the correctness of the response of the person. The person is anxious to know if he has given the right response by pressing the button and therefore continues to fixate steadily to the FBS. In this way the fixation of the eye to the FO/FBS is verified in order to provide saccade triggering stimulus STS to precisely known peripheral location.

The peripheral STS can be designed to mimic e.g. the standard stimuli used in conventional visual field examination devices. Thus its size, shape, duration and luminance can be chosen to conform to the standards for visual field examinations (ISO 12866: International standard for Perimeters). The STS can also be selected to resemble the FO, or any other character or object. A normal person's saccades to an unexpected peripheral stimulus normally take about 200 milliseconds (ms) to initiate, and then last from about 20-200 ms, depending on their amplitude. Therefore it takes in total about 200 ms-400 ms before the person has executed his or her saccade and redirected his or her fovea to the location of the peripheral STS. During this time the STS, can be replaced by a second fixation object ($FO_2$), which has the same design properties as the first fixation object ($FO_1$) and thus is only recognizable by foveal vision. When the person correctly identifies and reports the $FO_2$, we can assume that he has successfully performed an accurate saccade and redirected his or her fovea from $FO_1$ to $FO_2$, which in turn becomes the centre of the visual field. Immediately after or even when reporting the identification of $FO_2$, the sequence can be repeated using the new fixation object location of $FO_2$ as a centre of the visual field and providing a further peripheral STS.

The time period, i.e. reaction time (RT), or verified visual search reaction time (VVS-RT), for conducting the sequence from providing the STS (corresponding approximately to the time point of correctly reporting of the identification of the fixation object $FO_1$) to correctly reporting of the identification of $FO_2$ is rather constant for a person if the angular size and the other properties of the stimuli are kept constant. If, however, one location of the visual field has impaired vision (reduced sensitivity), the visibility (luminance) of the STS doesn't reach the threshold of detection and the initiation of the saccade fails. The saccade triggering stimulus is replaced after predetermined interval by second fixation object $FO_2$, which the person must then search using several saccades before he can correctly identify it. Thus the prolongation of the time period VVT-RT is an indication for impaired vision in that location of the visual field.

If this invention is used in visual field examination and the duration of the saccade triggering stimulus STS is 100 ms according to International Standard for Perimeters (ISO 12866), it is beneficial to have a brief interval of 100-200 ms before $FO_2$ is provided at the same location where the STS was provided in order to make it easier for the visual system to distinguish between the STS and the FO when the intensity of STS is very low.

Adjusting the length of the delay before $FO_2$ is provided can also be used to probe the time that is needed for the motor actions of the eye and/or head to shift his or her gaze direction from the location of $FO_1$ to STS. If a person has a abnormally slow saccades or otherwise difficulties with shifting his gaze direction, the time period between providing $FO_1$ and correctly reporting of the identification of it becomes shorter if the length of the delay before the $FO_2$ is provided is increased. This is discussed in more detail in the example 8.

Providing Saccade Triggering Stimuli to the Physiological Blind Spot

In many perimeters that are widely used nowadays, one way of checking if the person is steadily fixating the immovable fixation mark is to provide a test stimulus to the location of the visual field where the blind spot of the normal eye exists. If the alignment of the eye is correct, i.e. the eye is fixating the fixation mark, the person cannot see the test stimulus. If however the alignment is incorrect, the test stimulus is not any more inside the area of the blind spot and the person can see the flash and report seeing it by pressing the button.

In this invention the same principle can be applied with few unique modifications. Simultaneously or up to 300 ms after the person reports the identification of the FO and providing the STS, a blind spot saccade triggering stimulus $STS_{bs}$ and after that a blind spot distractor fixation object $FO_{bsd}$ is provided at the location at which the blind spot of the eye is. If the alignment of the eye is incorrect, i.e. the person does not fixate to the preceding fixation object $FO_p$ this results in that the $STS_{bs}$ becomes visible to the person and triggers the person to make a saccade to the location of the $STS_{bs}$ and reporting the identification of $FO_{bsd}$, which causes erroneous reporting in comparison to the true FO at the location where saccade triggering stimulus STS was.

Distracting and Misleading Fixation Objects

The human visual system is very efficient in conducting visual search. Therefore when performing examination according to this invention, the person sometimes finds and reports the FO with surprisingly short reaction time even if he has not detected the saccade triggering stimulus STS, which precedes the FO at the same location. If, as normally is the case, we want to examine the visibility of the STS with different luminance values, we might want to make finding of the FO more difficult for a person who has not detected the preceding STS. This can be done, according to this invention, by inserting visual search distractor fixation objects distinguishable from it by careful inspection, finding the FO among many $FO_{vs}$s solely by visual search without first detecting the STS becomes difficult and this makes the reaction time for reporting the correct identification of FO longer compared to the situation where FO is found with the help of detecting the STS.

Another means for making finding of the correct FO at the location where STS is provided more difficult, is to provide one or several fixation objects with a misleading pattern ($FO_m$) that causes the person, if he finds it with visual search in the case when STS was undetectable for him, to report an incorrect identification of the true fixation object FO which triggers a saccade towards FO.

Adjusting Brightness of Saccade Triggering Stimuli

The sensitivity of a given location of the visual field can be measured by repeating the sequence directed to a particular location of peripheral vision and by providing saccade triggering stimuli (STSs), which have different luminance values. When the luminance of the STS is reduced and it is approaching the threshold value of detection at a specified visual field location, the time period for the detection of the stimulus increases compared to stimuli that have luminance values that are clearly above the threshold. When the luminance of the STS is below the threshold value of a given location of the visual field, the STS is not visible to the person and gives no advance cue about the location of the fixation object (FO). This increases the reaction time for finding and identification of a FO and gives indication for the threshold for detection of STS of specified luminance.

Adjusting Brightness of Fixation Objects

The contrast sensitivity of the fovea can be measured by diminishing the brightness of the FO pattern. The threshold for visibility of the FO pattern can be detected when reaction time for correctly reporting the identification FO increases.

Fluctuation Between Persons

The time period from providing STS to correctly reporting the identification of $FO_2$ by e.g. pressing a correct button (=verified visual search reaction time WS-RT) can be divided to several phases which are controlled by various areas of the visual system and the brain and have differences in variation between individual persons:

(1) The time period for the detection of the STS in specific location of the visual field is dependable upon the sensitivity of the corresponding retinal location for that specific STS (e.g. depends on the size, duration, wavelength composition) and the adaptational state of the retina for the ambient illuminance. The influence of temporal integration and Pullfrich effect has been discussed above. When the STS is brighter than the threshold of the retina, a nerve stimulus travels through nerve paths to visual areas of the brain. This time period does not have much variation between persons, if the parameters mentioned above are kept constant.

(2) The time period for the initiation and execution of saccade to peripheral STS when the eye is fixating at a FO is controlled in the brainstem and cerebellum and has little variation between individuals.

(3) The time period for making corrective saccades: Saccades made to peripheral stimuli over 10 degrees in amplitude often undershoot the target by about 10%, and, after a short latency (about 150 ms), are followed by a corrective saccade to position the fovea precisely to the target, which in this invention can be replaced by a $FO_2$. Small saccades to peripheral stimuli under 10 degrees in amplitude often overshoot the target, which necessitates also some corrective saccades to position the fovea precisely to the target. This oculomotor function for making corrective saccades is also controlled in the brainstem and cerebellum. This time period has also little variation between individuals unless the neural areas and connections responsible for this function are defective.

(4) The time period for the identification of $FO_2$. This time period depends on the complexity of the $FO_2$. This time period can be brief and doesn't involve much cortical processing if $FO_2$ is visually very simple (e.g. distinct arrow). If $FO_2$ has a complex pattern, several small saccades processing are required before the pattern is recognized. Neural connections to the ventral stream of the brain to utilize visual memory of different patterns for recognition are required. The control of small corrective saccades requires also contribution from higher cortical brain areas. One example of this kind of pattern for FO could be a written word or words. This time period can be affected by a person's fatigue, wakefulness, alertness or various brain disorders.

(5) The time period for decision making when reporting the identification of $FO_2$ before any motor action for reporting the identification has been initiated. This time period is dependable on the difficulty of the task and can also have considerable variation between individuals.

(6) The time period for initiating and making the appropriate motor function by e.g. pressing the correct button with a finger. This time period has large variation between individuals.

In order to minimize the variation between individuals and to get more accurate measurements for time periods (1) to (3) it is beneficial, according to the invention, to separately measure the lengths of time periods 4 to 6 by providing further fixation object FFO at the same location as the previous fixation object FO and to measure the time period between correctly reporting the identification of FFO and FO. It is beneficial to use very simple visual stimuli for FO and FFO. When this time period is subtracted from the reaction time WS-RT, it enables comparing more accurately to corresponding time periods of normal persons because variance of the time periods between individuals is decreased.

Figure 9:
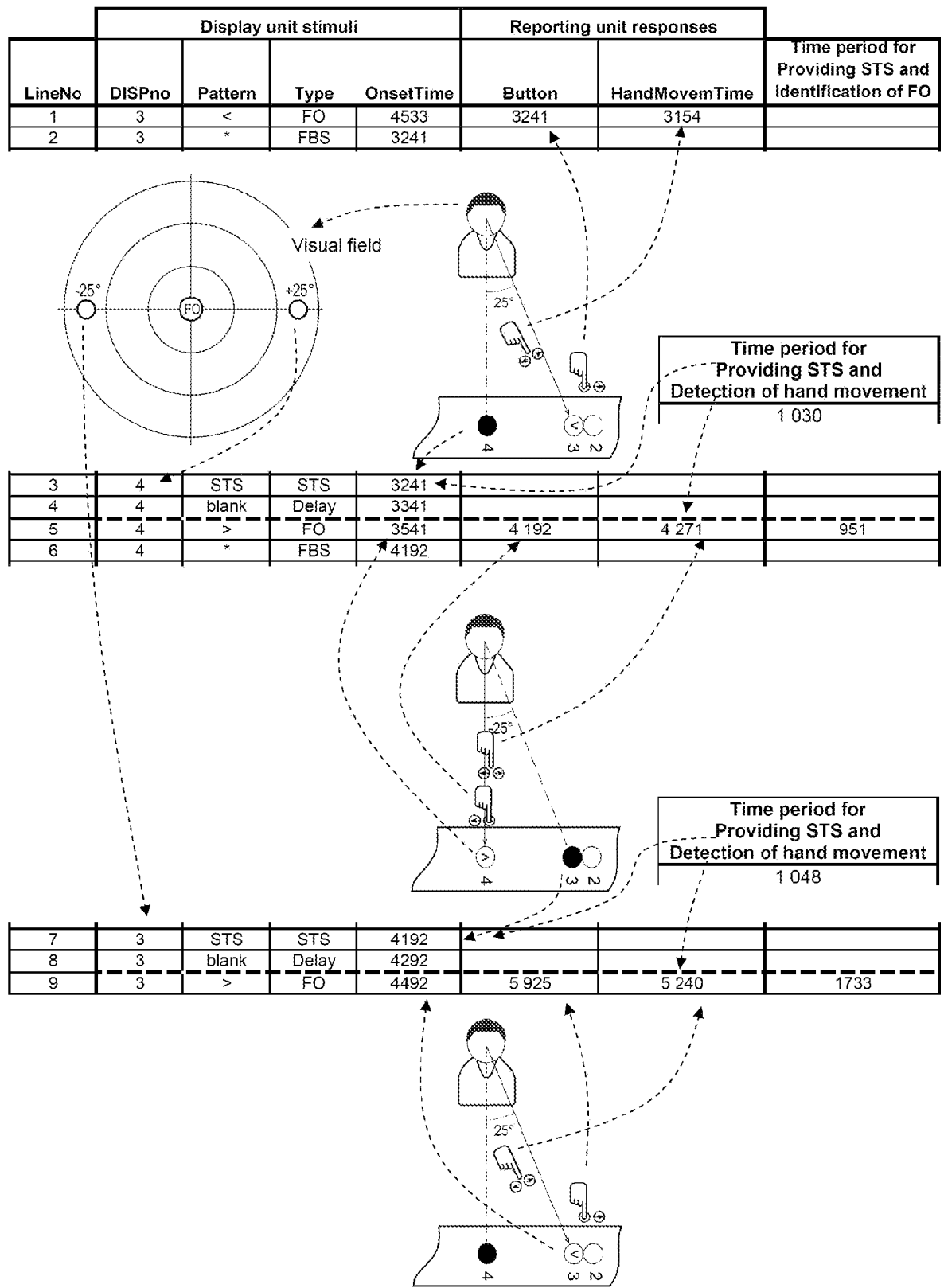
FIG. 9 illustrates a situation where a person has a normal visual field but defective saccades to the left but normal saccades to the right.

In the case when the person has defective ocular motor functions (e.g. slower than normal saccades to the left and normal saccades to the right, see example 7 and FIG. 9), the WS-RT is longer for STS which are displayed to the left compared to STS which are displayed to the right of the fixation of the eye even if the visual field of this person is normal and symmetrical. In order to distinguish if the prolongation of WS-RT results from defective ocular motor function or defective visual field, it is beneficial to ask the person at the same time when he makes a rapid eye movement, to point with his or her hand to the location of the STS as soon as he detects it. The initiation of the movement of the hand towards the STS can be monitored e.g. by a sensor that measures acceleration of the hand. This sensor can be an integral part of the response buttons of the person.

Background Luminance

The sensitivity of the retina to detect a saccade triggering stimulus STS depends on the adaptational state of retina to the ambient light of the room where the examination is conducted. In human eye this sensitivity of the retina obeys Weber law, which states that the discrimination threshold $\Delta l$ of the luminance of the stimulus is proportional to the intensity I of the background luminance ($\Delta l/I$=constant). Thus, if the sensitivity of the visual field location in a given background luminance is known, it is possible to calculate the threshold luminance for different background luminances by measuring the ambient luminance of the background where the stimulus is displayed with a suitable sensor or sensors mounted in the device. The measured and calculated ambient brightness in different areas of the display or displays can be compensated by adjusting the brightness of STS and FO stimuli accordingly.

Figure 13:
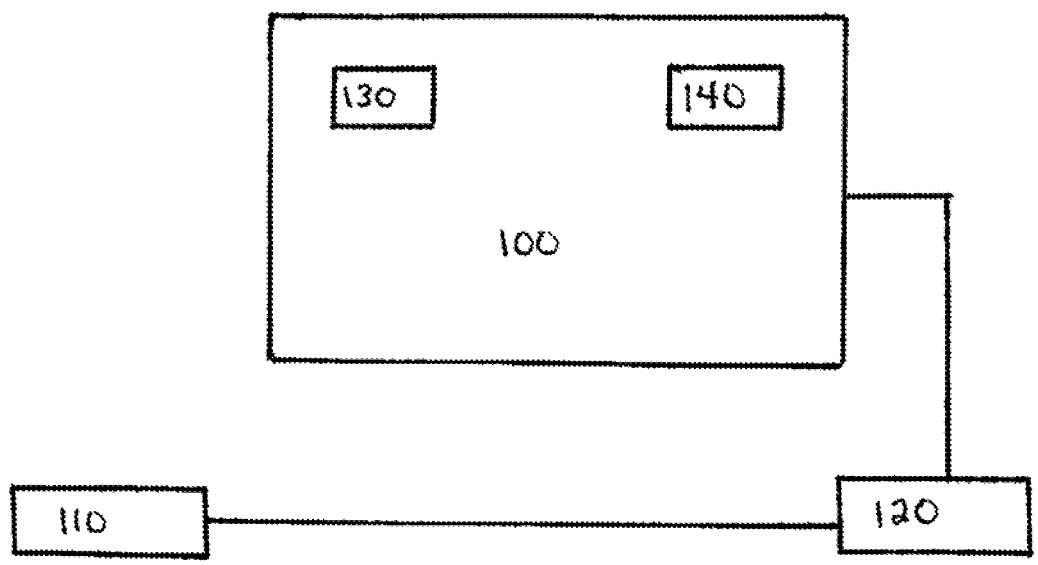
FIG. 13 is a schematic diagram which illustrates system having a display with two ambient light sensors.

FIG. 13 illustrates a display 100 having two ambient light sensors 130 and 140 in different areas of display 100. The display, including ambient light sensors 130 and 140, is operatively connected to data processing unit 120, which is also operatively connected to reporting means 110.

Smooth Pursuit

Smooth pursuit eye movements allow the eyes to closely follow a moving object so that the movements stabilize the projection of the moving target onto the fovea and corrects for any velocity error between eye and target. It is one of two ways that a person can voluntarily shift gaze, the other being saccadic eye movements. Smooth pursuit eye movement requires a moving visual stimulus, smooth pursuit triggering stimulus (SPTS). Pursuit is modified by ongoing visual feedback, which detects if the fovea is not aimed at the SPTS and initiates catch-up saccades to correct the aiming of the eye. The oculomotor system of the brain adjusts the angular velocity of smooth pursuit of the eye to match the velocity of moving stimulus SPTS to compensate for retinal slip of the SPTS. If the eye is accurately pursuing the SPTS and it is, according to the invention, replaced by a fixation object (FO), which is identifiable by the person only when the eye is accurately fixated on the FO, the person can quickly identify the fixation object FO and report the identification of it by e.g. pressing a correct button. If, however, the eye is not accurately aimed at the SPTS, the person cannot quickly recognize the FO but must make first a catch-up saccade or saccades or adjusts the velocity of smooth pursuit to aim the fovea accurately to FO for correct identification. Thus, the time period, from providing the FO to correctly reporting the identification of the FO, increases, if the smooth pursuit of the eye is not accurate.

Memory Guided Saccades

In addition to visually guided saccades, which are saccades elicited by peripheral visual stimuli (e.g. saccade triggering stimulus STS), human oculomotor system is capable also performing saccades towards a memorized location in the visual field. The present invention, in which the sequence of using the new fixation object location of $FO_2$ as a centre of the visual field and providing a further peripheral STS which in turn is replaced by further fixation object $FO_3$ in the same location as STS was, can be used to assess the ability to perform memory guided saccades as follows:

The sequence, using 3-6 different visual field locations, is displayed in predefined rhythm (e.g. new saccade triggering stimulus STS every second)

The sequence is practiced several times

At each step the identification of the fixation object FO is reported by the person.

After the practicing period the same sequence is displayed with the same rhythm but this time without the saccade triggering stimuli STS displaying only fixation objects FOs.

The person identifies the FOs by performing a sequence of saccades which are guided only by memory.

If the saccades are accurate, the fovea fixates accurately the fixation object in the sequence and it can be identified and reported by the person without any delay.

If the saccades are inaccurate and the fovea is fixating at different location as the FO in the sequence, several corrective saccades are required before the identification of the t FO is possible which causes delay in the reporting of the identification of FO.

Visual Ignition Interlock Device in a Power-Driven Vehicle

The invention can also be used as visual ignition interlock device installed in a motor driven vehicle when assessing if a person's fatigue, wakefulness or alertness, or use of alcohol or drugs makes him unfit for driving a power-driven vehicle. If the performance in conducting a visual search and visual decision making procedure utilizing this invention is inferior to normal values or inferior to person's own values obtained at earlier time point, the motor vehicle can not be started or the device will log the event, warn the driver and then start up an alarm.

Analysing Visual Attention of Individual Players in Team Games

The invention can also be used in sports related applications, e.g. in team games like soccer or ice hockey. A good player has the ability to observe other team members and to evaluate which of the team members are situated in good strategic locations on the playing field for passing the ball or puck. A novice player on the other hand easily concentrates too much on handling the ball or puck and accordingly observes the playing field and team members insufficiently. The invention can be used by the coach of the team when coaching a novice player to shift his attention to other team members. A display described in this invention can be attached to the player's head or hockey stick so that the coach of the team can light up a saccade triggering stimulus STS on the display of a player who is in a good strategic position in the playing field. The task of the novice player is to notice the STS and to report the identification of the fixation object FO, which is shown on the display unit of the team member, with a wireless response unit. The time points and the time periods of each of the players are recorded according to the invention. The coach can afterwards review the summary of the results of each individual player and track the development of the player's ability to make observations of his team members.

The Response Unit

In a preferred embodiment of a device for utilizing the method of the invention an electronic sensor for monitoring the acceleration, e.g. a motion sensing device, is installed in the response unit which the person holds with his or her hand.

Monitoring Movement of Head

In some cases, especially when examining children, the person cannot report the identification of the FO or detecting of the STS by pressing a button. In these cases it is preferable to monitor the movement of the head of the person with a movement or acceleration sensor attached to the head. The sensor can detect the movement of the head when the person detects the STS and tries to turn his eyes and head toward the STS.

The Device

Also a sensor or sensors for measuring the inclination angle of the device is preferably installed in the device, e.g. a display set, which is used for displaying the stimuli. Also a system for monitoring the distance to the eye of the person is preferably included. In a preferred embodiment of the device, distance monitoring can be done by the person who is assessing the function of the visual system by using electronic distance or proximity sensors, using optical distance meter based on double images produced by mirrors or in a simpler way by a neck strap which holds the device at fixed distance from the person.

When assessing the accuracy of smooth pursuit of the eye, a smooth pursuit triggering stimulus SPTS can be provided at one of the display units, e.g. at unit 1. The device or display unit is moved at desired velocity either manually or automatically. At irregular intervals a smooth pursuit triggering stimulus SPTS is replaced by a FO at the same display unit. If a person is accurately pursuing the moving SPTS, he can quickly identify the FO and report the identification by pressing a button.

DEFINITIONS

In this disclosure the term "visual system" refers to the part of the central nervous system which enables organisms to process visual detail, as well as enabling several non-image forming photoresponse functions. It interprets information from visible light to build a representation of the surrounding world. The visual system accomplishes a number of complex tasks, including the reception of light and the formation of monocular representations; the construction of a binocular perception from a pair of two dimensional projections; the identification and categorization of visual objects; assessing distances to and between objects; and guiding body movements in relation to visual objects. Visual system consists of: the eye, especially the retina, the optic nerve, the optic chiasma, the optic tract, the lateral geniculate body, the optic radiation, the visual cortex and the visual association cortex Referral to "does not comprise active monitoring of saccade or smooth pursuit of the eye of the person" and equivalent expressions mean in the context of this application that no direct means for monitoring the eye are involved. Means not relied on would include monitoring the eye visually with an optical telescope by the examiner, or with measuring eye motion by light, typically infrared, which is reflected from the eye and sensed by a video camera or some other specially designed optical sensor (video-oculography) or standard video camera. Other means monitoring the eye not relied on would be to use an attachment to the eye, such as a special contact lens with an embedded mirror or magnetic field sensor (search coil) or to measure the electric potentials originated from the eye with electrodes placed around the eyes (electro-oculogram, EOG). Instead the orientation of the eye to any FO is verified by the person himself by exploiting the unique psychophysical characteristics of the fovea centralis of the fundus of the human eye. By having the person immediately report identification of any FO when having fixated the eye to such a FO the fixation of the eye at specific time points of identification can be verified.

In this disclosure the term "person" refers to the individual whose function of the visual system is assessed or practised. Likewise "eye", "visual field", "oculomotor functions", "saccade" and "smooth pursue" refers to the person.

The term "fovea" is the region with the highest visual acuity of the retina of the eye.

The term "fixation object" is a visible target where the line of sight (visual axis) or the fovea centralis of the retina of the eye is aimed at, or fixates and it typically consists of a small character, symbol or pattern.

The term "visual field" refers to the physical objects and light sources in the external world that impinge the retina of the eye of the person. The term "standard visual field coordinate system" refers to reference system for designating locations in the visual field, and which is in wide use in the field of visual field examination and is also referenced in the International Standard for Perimeters (ISO 12866). In this system the pupil of the eye is located in the origin of the spherical coordinate system. The location of any visual field locus is specified by the half-meridian e and the eccentricity Φ of the center of the test stimulus, both expressed in degrees (Θ, Φ). The zero-degree half-meridian is defined to the right of the patient (as seen by the patient). The specified half-meridian then proceeds anticlockwise through 360° about the fixation stimulus (as seen by the patient). The fixation point is defined as having 0° eccentricity.

The term "meridian" refers to two half-meridians constituting one straight line in the visual field coordinate system through the origin. It's direction in the visual field coordinate system is specified by either of the half-meridians.

The term "blind spot" or "physiological blind spot" is the area in the visual field that corresponds to the lack of light-detecting photoreceptor cells on the optic disc of the retina where the optic nerve passes through it. Since there are no cells to detect light on the optic disc, a part of the field of vision is not perceived. The blind spot is located about 12-15° temporal and 1.5° below the horizontal and is roughly 7.5° high and 5.5° wide.

The term "contrast" is the difference in luminance and/or colour of the foreground and background of the object that makes an object (or its representation in an image or display) distinguishable.

The term "contrast sensitivity" is a measure of the ability of the visual system to detect contrast.

The term "saccade" is a fast movement of the eye from one fixation object to a target which is located somewhere within the visual field of the eye in order to correct for a position error between eye and target.

The term "saccade triggering stimulus, STS" is a visible target within the visual field which elicits a saccade which redirects the fovea or line of sight from fixation object FO to the STS. If anti-saccade paradigm is used the target for a saccade is at the symmetrical location of the STS in relation to FO or origin of the visual field.

The term "smooth pursuit" refers to a slow eye movement that stabilizes the projection of the moving target onto the fovea and corrects for any velocity error between eye and target.

The term "feedback stimulus, FBS" refers to a character, symbol or pattern which is displayed at the same location as fixation object FO. It gives visible feedback about the correctness of the reported identification of the fixation object FO.

The term "further fixation object, FFO" refers to a fixation object, which is provided to the same location as the fixation object which preceded the FFO.

The term "interrupting fixation stimulus, IFS", refers to a character, symbol or pattern which is displayed at the same location as the preceding fixation object FO or FFO before the next FFO is displayed. It can serve as a feedback stimulus, FBS, to give feedback about the correctness of reported identification of preceding fixation object FO of FFO.

The term "verified visual search reaction time, WS-RT" refers to time period for conducting the sequence from providing the STS to correctly reporting of the identification of second fixation object $FO_2$ which is provided at the same location as STS.

Preferred Embodiments of the Invention

Many preferred embodiments of the method of the invention further comprise g) providing a further fixation object $FFO_i$ identifiable by the person only when the eye or eyes is accurately fixated on said $FFO_i$, i.e. when said $FFO_i$ is positioned at the fovea of said eye or eyes of said person, provided at the same location as that of an immediately preceding further fixation object $FFO_p$, preferably with a short interrupting fixation stimulus $IFS$ at said same location between provided sequential further fixation objects FFOs, h) having said person identify said $FFO_i$, said identification referred to as an identification of said $FFO_i$, i) having said person report said identification of $FFO_i$, j) recording correctness of reported identification of said FFO; and time point of providing said FFO; and time point of reporting of identification of $FFO_i$, and k) calculating time periods between providing $FFO_i$ and said reporting of identification of said $FFO_i$;

wherein said time period is subtracted from the time periods calculated in step f) of claim 1 to estimate the time period between providing said STS and accurate fixation of said eye or eyes of said person on said FO, and/or providing said FO and accurate fixation of said eye or eyes of said person on said FO, if said SPTS is employed;

to enable comparing said time periods to corresponding time periods regarded normal for persons corresponding to said person or previously normal for said person.

In many preferred embodiments of the method of the invention a feedback stimulus FBS, giving visible feedback about the correctness of the report by the person of the identification of a fixation object FO, is provided at the location of said FO reported, immediately after, i.e. within 100 ms, preferably 30 ms, more preferably 10 ms and most preferably within 3 ms, said person has reported identification of said FO.

Some preferred embodiments of the method of the invention comprise a multitude of cycles comprising the following sequential steps:

i) having the eye or eyes of the person fixate on a first fixation object $FO_1$ identifiable by the person only when said eye or eyes is accurately fixated on $FO_1$, i.e. when said $FO_1$ is positioned at the fovea of said eye or eyes of said patient, ii) having said person identify, said identification referred to as first identification, said $FO_1$, iii) having said person report said first identification, iv) providing a first saccade triggering stimulus $STS_1$ within visual field of said eye or eyes accurately fixated to said $FO_1$ of said person, at a different location of the visual field of said patient than said $FO_1$, v) having said eye or eyes of said person execute a saccade in response to a saccade triggering stimulus $STS_1$, said saccade referred to as first saccade of said eye or eyes, vi) providing during said first saccade or immediately thereafter a second fixation object $FO_2$ at a location of said $STS_1$;

repeating steps i) to vi) for each said cycle wherein in each repetitive cycle said $FO_1$ is said $FO_2$ of a previous cycle;

wherein method said identifications reported, and time points of providing said $STS_1$, time points of providing said $FO_2$ and said reporting times of each cycle are recorded; time periods between providing said $STS_1$ or $FO_2$, and said reporting of identifications of said $FO_2$ are calculated;

wherein an incorrectly reported or missing identification, and/or extended delay in a correctly reported identification, compared to delay regarded normal for persons corresponding to said person, or compared to delays for other locations of the visual field of said eye or eyes of said person, or compared to delays of said person obtained at earlier time point in his or her life, are markers for an abnormal and/or deteriorated ability of said eye or eyes of said person to detect said STS at said specific location of said visual field of said eye or eyes of said person, ability of said eye or eyes of said person to accurately hit a target by executing a saccade triggered by said saccade triggering stimulus STS, ability of said person to identify said FO, and/or function of said visual system of said person.

Typically the second fixation object $FO_2$ is provided after a delay, preferably a delay of 50-1000 ms, after termination of the first saccade triggering stimulus $STS_1$.

Typically the delay of providing the second fixation object $FO_2$ after termination of the first saccade triggering stimulus $STS_1$ differs between the cycles, being preferably between 50-1000 ms. In such embodiments the duration of the saccade and fixation can be obtained by defining the minimum delay in providing the second fixation object $FO_2$ after termination of the first saccade triggering stimulus $STS_1$, resulting in the shortest calculated time period between providing said $FO_2$ and correctly reporting the identification of said $FO_2$ when providing a $STS_1$, with a defined intensity and duration at a defined location of the visual field of the eye or eyes of the person.

In many preferred embodiments the intensities of the saccade triggering stimuli STSs differ between the cycles, being between intensities that are not visible to the eye or eyes of the person at any location of the visual field, preferably zero, and intensities high enough for said person to respond to said saccade triggering stimulus STS independent of the intensity of the STS.

In some preferred embodiments reporting an incorrect result when identifying the fixation object FO results in providing a new fixation object $FO_n$, preferably preceded by a new saccade triggering stimulus $STS_n$, at the same physical location as the erroneously identified fixation object $FO_n$; before providing a saccade triggering stimulus STS at a different physical location.

In some preferred embodiments a blind spot saccade triggering stimulus $STS_{bs}$ is provided essentially simultaneously, preferably between 0 ms and 300 ms after reporting of an identification of a preceding $FO_p$, with the saccade triggering stimulus STS intended to trigger execution of a saccade of the eye or eyes of the person, wherein said $STS_{bs}$ is provided at the location at which the blind spot of the visual field of the eye or eyes of the person is when said eye or eyes is fixated at the preceding fixation object $FO_p$. In such embodiments a blind spot distractor fixation object $FO_{bsd}$ is typically provided at the location of the blind spot saccade triggering stimulus $STS_{bs}$.

In many preferred embodiments one or more visual search distractor fixation objects $FO_{vs}$ and/or misleading fixation objects $FO_m$ are provided at selected locations of the visual field of the eye or eyes of the person essentially simultaneously with, preferably not earlier than 500 ms before and not later than 1000 ms after, the fixation object FO at the location of the saccade triggering stimulus STS, wherein the $FO_{vs}$s are distinguishable from the FO provided at the location of the STS.

In some embodiments of the invention the method of the invention comprises evaluating the accuracy of smooth pursuit of the eye and/or eyes of a person, said smooth pursuit being triggered by a smooth pursuit triggering stimulus SPTS;

by i) having said eye or eyes of said person smoothly pursue in response to said SPTS, ii) providing a fixation object FO which object is identifiable by the person only when said eye or eyes is accurately fixated on said FO, i.e. when said FO is positioned at the fovea of said eye or eyes of said person, at a location whereto said eye or eyes of said person is expected to be fixated during said smooth pursuit and said FO moving at the same angular velocity and direction as said SPTS, iii) having said person identify said FO, said identification referred to as an identification of said FO, iv) having said person report said identification of said FO, v) recording correctness of reported identification of said FO and time points of providing said FO, and reporting of identification of said FO, vi) calculating time period between providing said FO and reporting of said identification of FO, wherein an incorrect reporting or missing identification, and/or extended delay in reporting of a correct identification, compared to delay regarded normal for persons corresponding to said person or said person, are markers for an abnormal and/or deteriorated accuracy of smooth pursuit of said eye or eyes of said person.

In preferred embodiments of the invention the method of the invention does not comprise active monitoring of saccades, if saccade triggering stimuli STSs are employed; and/or smooth pursuit, if smooth pursuit triggering stimuli SPTSs are employed, of the eye or eyes of said person.

Preferred embodiments of the use according to the invention include use wherein the software of the data processing unit is also for recording the locations of the saccade triggering stimuli STSs provided, preferably for different tilt angles of the device, in a standard visual field coordinate system with its origin located at the centre of the visual field.

Some preferred embodiments of the system of the invention comprise a display set with a multitude of displays, preferably from 3 to 100 displays, more preferably from 4 to 30 displays, even more preferably from 20 to 30 displays and most preferably 24 displays. The smaller the displays the more displays are typically employed. The larger the displays the less displays are typically employed. If a small system is preferred a multitude of small displays, typically in a set, are employed. In small systems the displays, typically in a display with a multitude of displays, are very small, the size preferably being from 0.2" to 5", more preferably 0.5" to 2" and most preferably about 1".

Some preferred embodiments of the system comprise one display, displays or a display set wherein the size of the display or displays are from 12" to 168", preferably from 20" to 112", more preferably 32" to 84", and most preferably from 40" to 55".

Typically the display or displays are each capable of displaying at least the saccade triggering stimuli STS and the fixation object FO, and preferably also smooth pursuit triggering stimulus SPTS, further fixation object FFO and feedback stimulus FBS. In some embodiments the displays are in a row being parallel with the longitudinal axis of the display set. In some of the preferred embodiments the displays are positioned in the parallel row so that, when the display unit is placed at the distance, intended to be employed when evaluating an eye of a person, from said eye to be evaluated, the display units, when facing said eye and perpendicular to the optical axis of said eye fixated at said display unit, are at different eccentricity angles of the optical axis of the eye, when fixated to said display units, applicable for intended evaluation. Typically the different display units are at eccentricity angles of 0, 5, 15, 25, 35, 75 and 90 degrees relative to the display unit furthest at one end of the display set, and preferably an additional display unit at an eccentricity angle of 23 degrees relative to said display unit furthest at one end is included. Another typical set of eccentricity angles for display units is 0, 10, 15, 40, 70 and 90 degrees.

In many preferred embodiments the display or displays are positioned so that, when the display unit is placed at the distance, intended to be employed when evaluating an eye or eyes of a person, from said eye or eyes to be evaluated, the display units, when facing said eye or eyes fixated at said display unit can display saccade triggering stimuli STSs and/or fixation objects FOs at different eccentricity angles of the visual axis of the eye or eyes, when fixated to any of said FOs of said display or displays, applicable for intended evaluation.

In many preferred embodiments of the system of the invention the display, displays or display set comprise a position sensor or sensors enabling confirmation of the display, displays or display set being perpendicular to the optical axis of the eye, and/or eyes, to be evaluated and/or the angle with which the longitudinal axis of the display, displays or display set deviates, either to the left or right, from the upright position.

Some preferred embodiments of the system comprise displays as mentioned above but arranged in two dimensions in order to cover the whole visual field, in which case the number of displays may be large, preferable more than 50. Alternatively the system may consist of one or more large displays, which are capable of displaying at minimum the STS and FO in many different physical locations in either one or two dimensions.

Some preferred embodiments of the system comprise at least one, preferably 2 or more, sensors for monitoring the distance between said display, displays or display set and the eye or eyes of said person.

In many preferred embodiments of a the system of the invention also at least one sensor, preferably 2 or more sensors, for monitoring the ambient illumination of the room where the measurements are being conducted is comprised in the system, preferably in the display, displays or display set of the system.

Preferred embodiments of the system comprise means for adjusting the brightness of the STS and/or FO.

Preferred embodiments of the system comprise a sensor or sensors to be attached to the head of the person, wherein said sensor or sensors can detect the speed, timing or/and the angle of rotation of the head when displaying saccade triggering stimuli in the visual field of the person.

Preferred embodiments of the system do not comprise means for active monitoring of saccades, if saccade triggering stimuli STSs are employed; and/or smooth pursuit, if smooth pursuit triggering stimuli SPTSs are employed, of the eye or eyes of said person.

Preferred embodiments of the software product of the invention further comprise means for recording the locations of the saccade triggering stimuli STSs provided in standard visual field coordinate system of the eye or eyes of the person.

Preferred software products of the invention comprise means for determining for each intensity of saccade triggering stimuli STSs and/or fixation objects FOs the margin of error of the results provided employing the software product.

EXAMPLES

The following experimental section illustrates the invention by providing examples.

Example 1

Device

Figure 2:
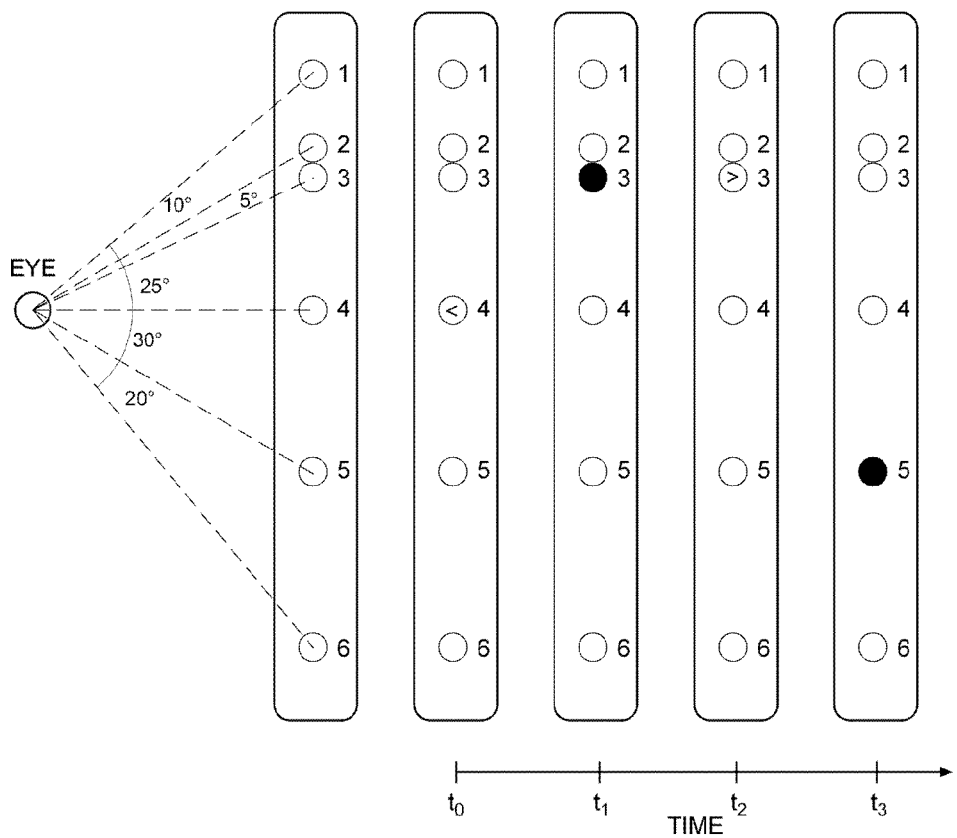
FIG. 2 illustrates an embodiment of the device with display units 1-6 in a one-dimensional array for simplicity and an example of a sequence of the method of the present invention.

A preferred embodiment of a device for utilizing the method of the invention consists of a display unit, which is capable of providing both fixation object FO, which is designed so that it is only detectable by foveal vision, and saccade triggering or smooth pursuit triggering stimuli (STS or SPTS) which are designed to the needs of the function of the visual system which are being assessed or practised. In the preferred embodiment several display units can be used (FIG. 2) They can be located at various angular distances in relation to the eye of a person. In FIG. 2, consecutive angular distances 10, 5, 25, 30, and 20 degrees are used. According to this invention, the eye makes saccadic eye movements between display units 1-6. Table 1 summarizes all the possible saccades which the eye can make between the six display units. In Table 2 all possible angular distances are arranged in order.

FIG. 2 illustrates a sequence of an examination according to the invention: At time point $t_0$ a fixation object FO is provided at display unit 4. When the person correctly identifies and reports the FO at time point $t_1$, a saccade triggering stimulus STS is provided at display unit 3, which is located 25 degrees from display unit 4. At time point $t_2$ a second fixation object $FO_2$ is provided at display unit 3. At time point $t_3$, when the person correctly identifies and reports the $FO_2$, a saccade triggering stimulus STS is provided at display unit 5, which is located 55 degrees from display unit 3.

TABLE 1

Angular distances in degrees between the different displays (1-6; FIG. 2) when device is placed perpendicular to the axis of vision at the recommended distance for the particular device.

|   | 1 | 2 | 3 | 4 | 5 | 6 |
|---|---|---|---|---|---|---|
| 1 | 0 | −10 | −15 | −40 | −70 | −90 |
| 2 | 10 | 0 | −5 | −30 | −60 | −80 |
| 3 | 15 | 5 | 0 | −25 | −55 | −75 |
| 4 | 40 | 30 | 25 | 0 | −30 | −50 |
| 5 | 70 | 60 | 55 | 30 | 0 | −20 |
| 6 | 90 | 80 | 75 | 50 | 20 | 0 |

TABLE 2

All angular distances in degrees covered (see Table 1) by
the display placement of the device of FIG. 2

| 5 | 10 | 15 | 20 | 25 | 30 | 40 | 50 | 55 | 60 | 70 | 75 | 80 | 90 |
|---|----|----|----|----|----|----|----|----|----|----|----|----|----|
| −5 | −10 | −15 | −20 | −25 | −30 | −40 | −50 | −55 | −60 | −70 | −75 | −80 | −90 |

Example 2

Evaluation of Visual Field

Figure 3:
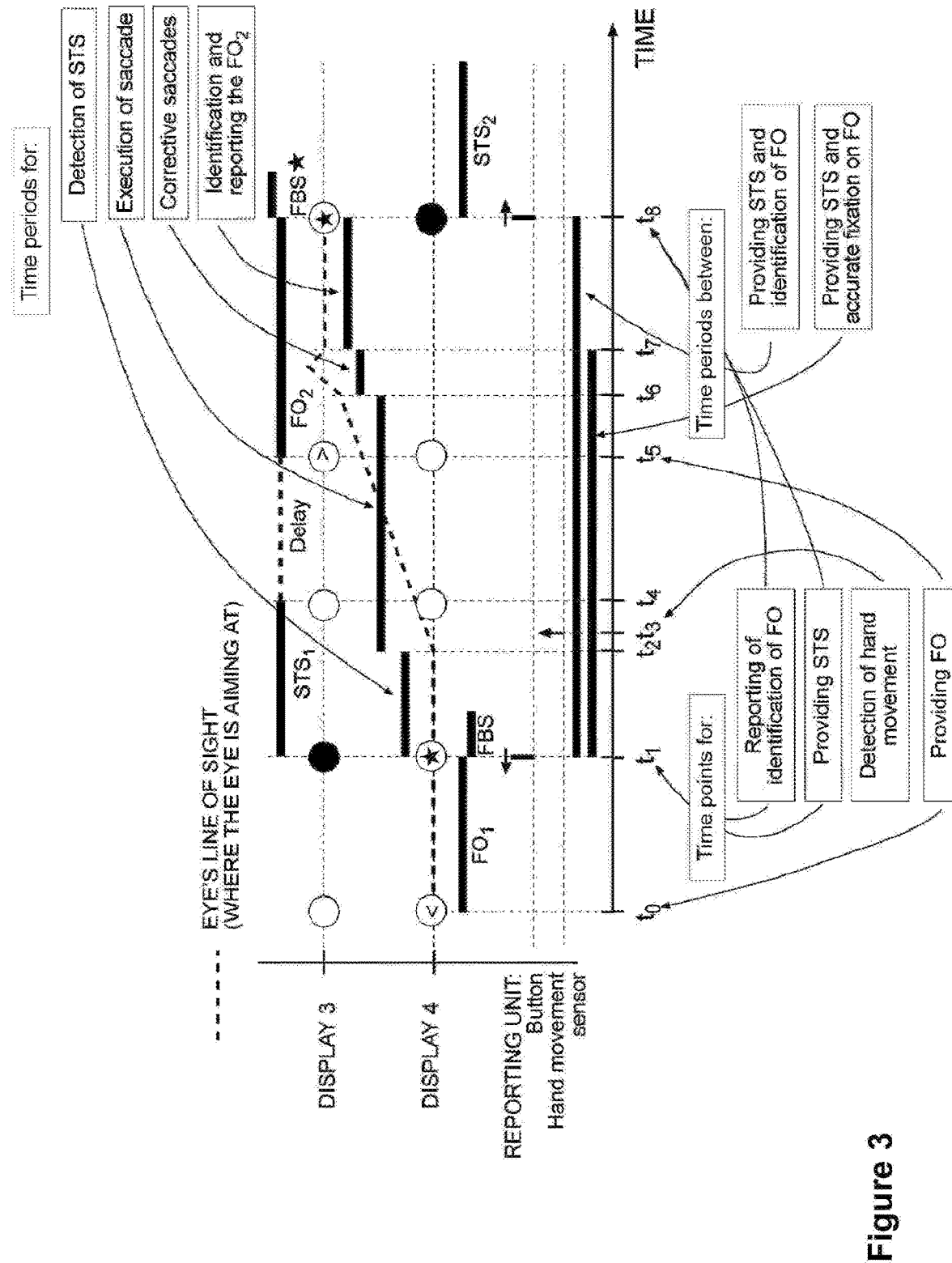
FIG. 3 illustrates several phases and time points of a sequence for evaluating the eye of a person.

Evaluation of the visual field of an eye of a person can be carried out e.g. as follows (see FIG. 3):

The sequence illustrated in FIG. 3 starts with providing a saccade triggering stimulus $STS_1$ and ends in correctly reporting the identification of $FO_2$. Only display units 3 and 4 (see FIG. 2) are visible in this illustration. The responses of the person are also illustrated: the movement of the hand towards the display unit is recorded by a hand movement sensor and choice of the button the person has pressed reports the identification of the fixation object FO.

Fixation object $FO_1$ is provided at display unit 4 at time point $t_0$. When a person identifies it (an arrow to the left) and reports by pressing a correct button (left button) at time point $t_1$, the fixation object $FO_1$ is extinguished and a saccade triggering stimulus $STS_1$ is provided at display unit 3 which is located 25 degrees apart from display unit 4. If standard visual field examination is being performed, the size, shape, duration and luminance of the STS can be chosen to conform to the standards for visual field examinations (ISO 12866: International standard for Perimeters). In such a case the duration of STS is 100 ms after which it is extinguished at time point $t_1$ and a brief delay interval of 100-200 ms can be used before a second fixation object $FO_2$ is provided at the same display unit 3 at time point $t_5$. When a person identifies it (an arrow to the right) and reports by pressing a correct button (right button) at time point $t_0$, the fixation object $FO_2$ is extinguished and a saccade triggering stimulus $STS_2$ is provided again at display unit 4. This cycle can be repeated using different display units as required to collect time points for all the visual field locations needed and varying the parameters of STS and FO as needed to measure e.g. the threshold value for detection of STS in specified visual field location. In FIG. 2 the orientation of the device is vertical and therefore only visual field locations in this vertical meridian can be measured. Visual field locations in different meridians can be measured by tilting the orientation of the device to desired inclination.

Figure 5:
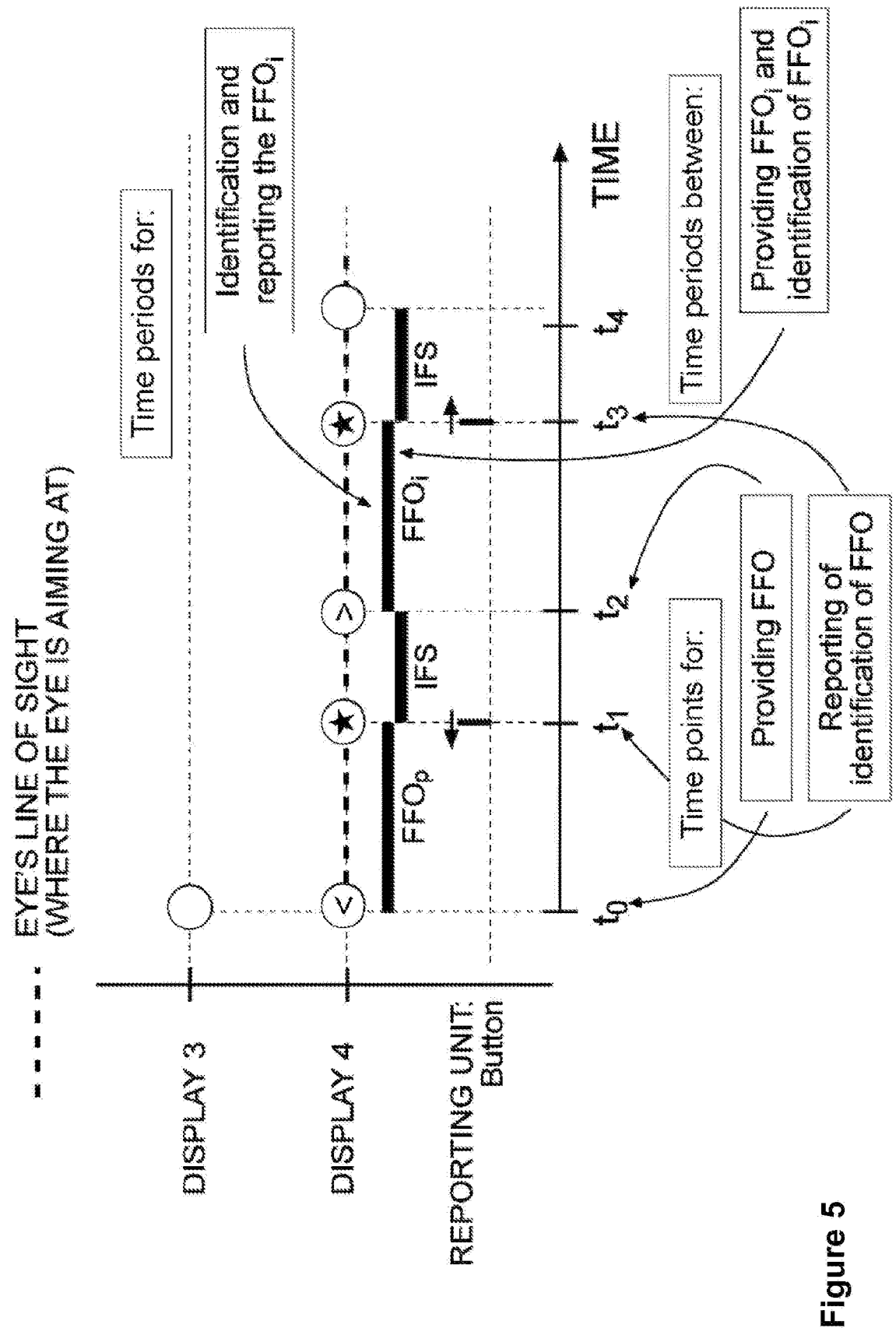
FIG. 5 illustrates the phases and time points of the sequence of providing several consecutive further fixation objects FFO to the same display.

The time period for identification and reporting the fixation object (see FIG. 3, the time period between time points $t_8$ and $t_7$) can be measured separately without any eye movements e.g. as follows (see FIG. 5):

To the display unit 4 at time point $t_0$ a further fixation object $FFO_p$ is provided which the person correctly identifies by pressing the correct button at time point $t_1$. Interrupting fixation stimulus IFS optionally replaces the $FFO_p$ and optionally gives the person a visible feedback about the correctness of the reporting the identification of $FFO_p$. At time point $t_2$ a further fixation stimulus $FFO_i$ replaces the IFS and the person correctly identifies it by pressing the correct button at time point $t_3$. The time period between providing $FFO_i$ ($t_2$) and identification and reporting of $FFO_i$ ($t_3$) reflects nearly the same visual and motor processes as the time period between $t_8$ and $t_7$ in FIG. 3 (identification and reporting of $FO_2$). For estimating the time period between providing STS and accurate fixation on fixation object $FO_2$ (see FIG. 3, time period between $t_7$ and $t_1$) the time period between $t_3$ and $t_2$ in FIG. 5 can be subtracted from the time period between $t_8$ and $t_1$ in FIG. 3 (time period between providing STS and identification and reporting of $FO_2$). The accuracy of the time periods can be increased by repeating the sequences several times so that mean of several measurements can be calculated.

Example 3

Distracting Fixation Objects

Figure 4:
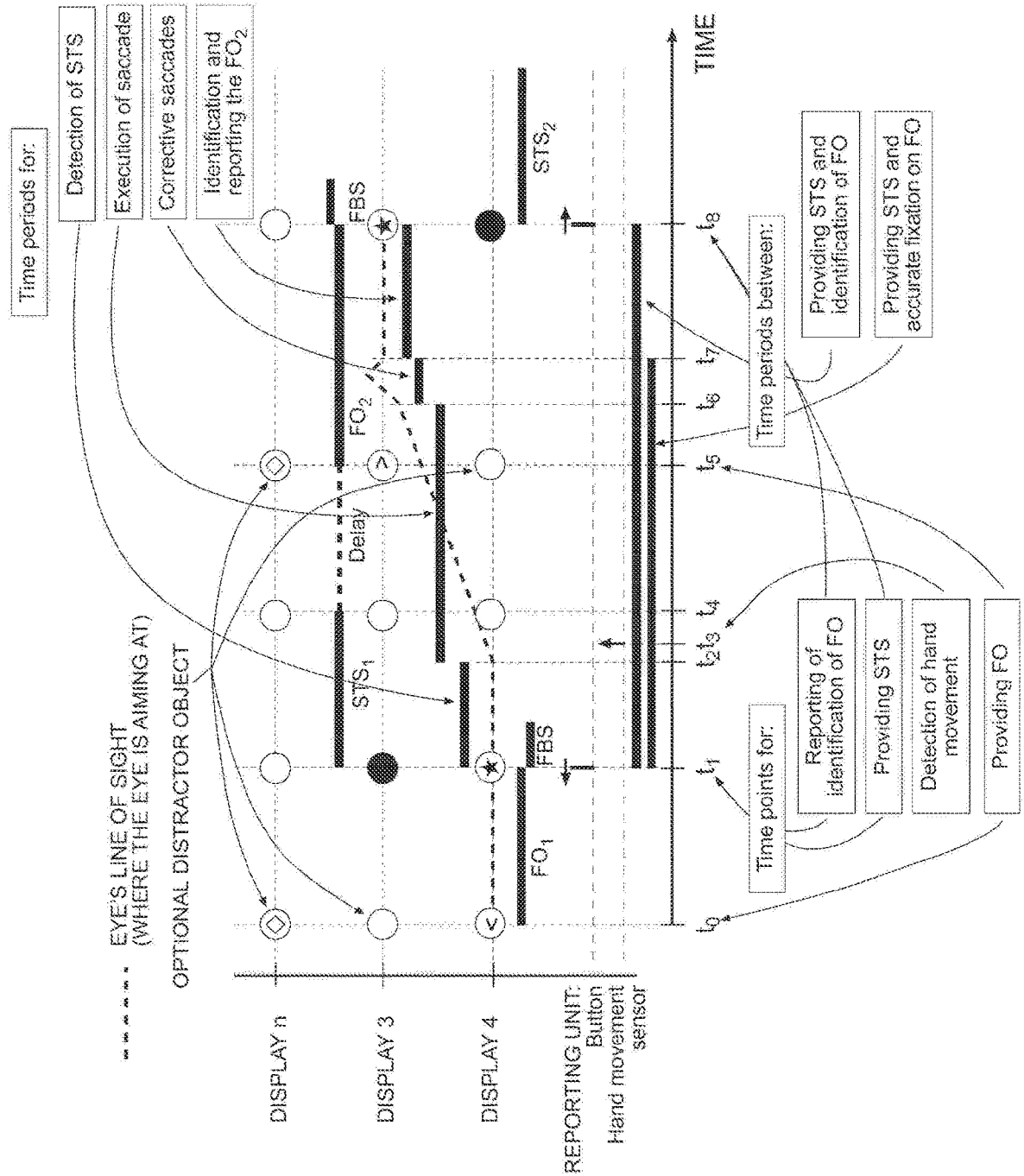
FIG. 4 illustrates the use of visual search distractor objects.

FIG. 4 illustrates the use of visual search distractor fixation objects (named 'distractor object' in FIG. 4). At time point $t_5$ one or many optional distractor objects are provided to the display unit(s) n in addition to $FO_2$ provided to the display unit 3. If the person has detected saccade triggering stimulus $STS_1$ and has made a saccade toward display 3, he or she finds easily and without delay the $FO_2$ and reports the identification of it. Because the distractor objects resemble FO but are distinguishable from it by careful inspection, finding the FO among many distractor objects solely by visual search without detecting first the STS becomes difficult and makes the reaction time for reporting the correct identification of FO longer compared to the situation where FO is found with the help of detecting the STS which triggers a saccade towards FO.

TABLE 3

Results from measuring the time period for identification and reporting the fixation object (see FIG. 4):

| | | | Display unit stimuli | | | | | Reporting unit responses | | | Time period for Providing FFO and identification of FFO |
|---|---|---|---|---|---|---|---|---|---|---|---|
| LineNo | DISPno | Pattern | Direction | Intensity | Duration | Type | Onset-Time | Button | Accuracy | Response Time | |
| 1 | 4 | > | right | 30 | | FO | 4 533 | right | 1 | 5 451 | |
| 2 | 4 | # | | 200 | 100 | IFS | 5 451 | | | | |
| 3 | 4 | < | left | 30 | | FFO | 5 551 | left | 1 | 6 076 | 525 |
| 4 | 4 | # | | 200 | 100 | IFS | 6 076 | | | | |
| 5 | 4 | > | right | 30 | | FFO | 6 176 | right | 1 | 6 746 | 570 |
| 6 | 4 | # | | 200 | 100 | IFS | 6 746 | | | | |
| 7 | 4 | < | left | 30 | | FFO | 6 846 | left | 1 | 7 398 | 551 |

TABLE 3-continued

Results from measuring the time period for identification and reporting the fixation object (see FIG. 4):

| | | | Display unit stimuli | | | | | Reporting unit responses | | | Time period for Providing FFO and identification of FFO |
|---|---|---|---|---|---|---|---|---|---|---|---|
| LineNo | DISPno | Pattern | Direction | Intensity | Duration | Type | Onset-Time | Button | Accuracy | Response Time | |
| 8  | 4 | # |       | 200 | 100 | IFS | 7 398  |       |   |        |     |
| 9  | 4 | > | right | 30  |     | FFO | 7 498  | right | 1 | 8 093  | 596 |
| 10 | 4 | # |       | 200 | 100 | IFS | 8 093  |       |   |        |     |
| 11 | 4 | > | right | 30  |     | FFO | 8 193  | left  | 0 | 8 291  |     |
| 12 | 4 | # |       | 200 | 100 | IFS | 8 291  |       |   |        |     |
| 13 | 4 | > | right | 30  |     | FFO | 8 391  | right | 1 | 8 937  | 546 |
| 14 | 4 | # |       | 200 | 100 | IFS | 8 937  |       |   |        |     |
| 15 | 4 | < | left  | 30  |     | FFO | 9 037  | left  | 1 | 9 551  | 514 |
| 16 | 4 | # |       | 200 | 100 | IFS | 9 551  |       |   |        |     |
| 17 | 4 | < | left  | 30  |     | FFO | 9 651  | left  | 1 | 10 158 | 507 |
| 18 | 4 | # |       | 200 | 100 | IFS | 10 158 |       |   |        |     |
| 19 | 4 | < | left  | 30  |     | FFO | 10 258 | left  | 1 | 10 786 | 528 |
| 20 | 4 | # |       | 200 | 100 | IFS | 10 786 |       |   |        |     |
| 21 | 4 | > | right | 30  |     | FFO | 10 886 | right | 1 | 11 420 | 534 |
| 22 | 4 | # |       | 200 | 100 | IFS | 11 420 |       |   |        |     |
|    |   |   |       |     |     |     |        |       |   | Mean:  | 541 |

Example 4

Sequence of Examination with Further Fixation Object

Figure 6:
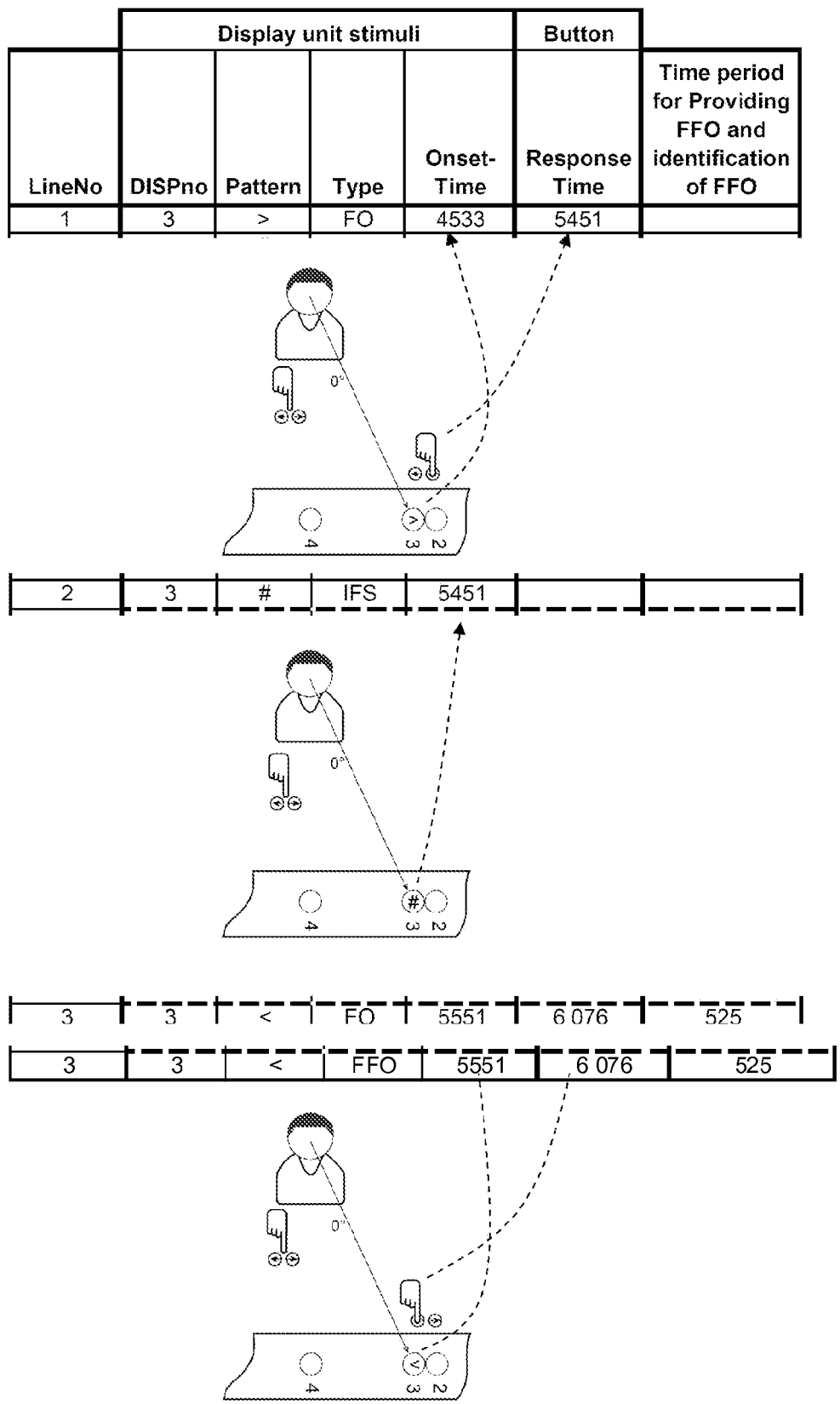
FIG. 6 illustrates a sequence of an examination wherein a further fixation object has been provided to the same display unit as a preceding fixation object.

FIG. 6 illustrates an embodiment according to claim 2. In the figure the results of an examination are presented where a further fixation object FFO has been provided to the same display unit (display unit 3, LineNo 3) as the preceding fixation object (LineNo 1). Brief, duration 100 ms, interrupting fixation stimulus IFS (LineNo 2) has been provided between the two fixation objects. In this case the time period between providing FFO and identification of FFO is 525 ms. This kind of stimulus presentation does not need any ocular movement because further fixation objects are located at visual axis (foveal). See FIG. 5 for presentation of this type of examination as a schematic timeline and table 3 for more complete data set of the examination.

Example 5

Sequence of Examination of One Location of Visual Field

Figure 7:
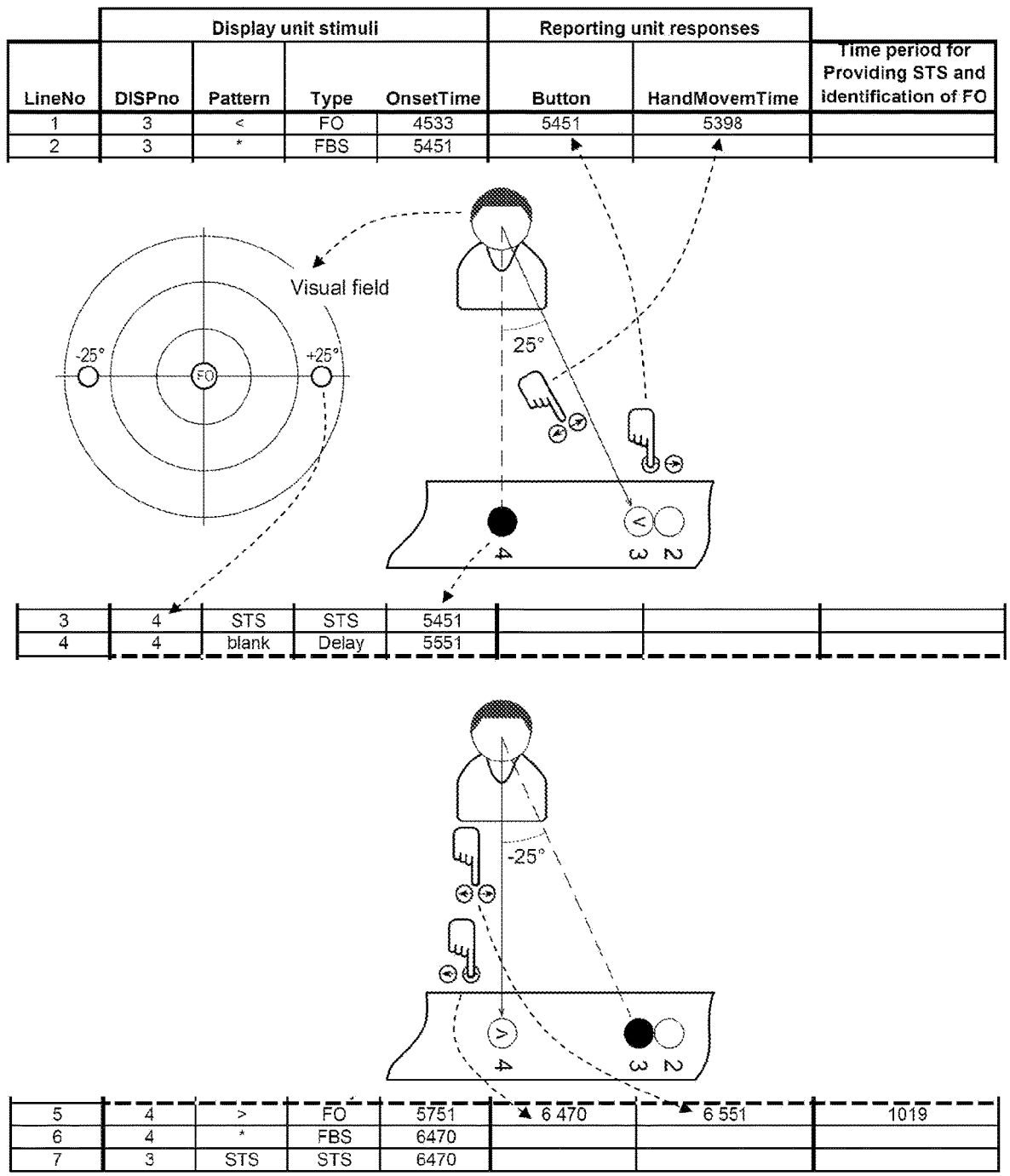
FIG. 7 illustrates a sequence of an examination of one location of visual field.

FIG. 7 illustrates a sequence of an embodiment according to claim 1. In the figure an example of an examination of one location of visual field (25° peripherally to the right from the fixation or the centre of the visual field) is presented. When the eye is fixating on the fixation object FO at display unit 3 and the person reports the identification of FO by pressing the button at time point 5451 ms (LineNo 1), a saccade triggering stimulus STS (duration 100 ms) is provided to the display unit 4, which is located 25° to the right from the display unit 3. This stimulus is detected by corresponding peripheral visual field location and triggers a saccade towards display unit 4. At time point 6470 ms (LineNo 5) the person correctly reports the identification of the fixation object which is provided to the display unit 4 after a delay of 200 ms (LineNo 4) at time point 5751 ms (LineNo 5). The time period for providing STS (LineNo 3) and identification of FO by pressing the button (LineNo 5) in this case is 1019 ms. See FIG. 3 for presentation of this type of examination as a schematic timeline.

Example 6

Sequence of an Examination where a Person with Defective Visual Field Location

Figure 8:
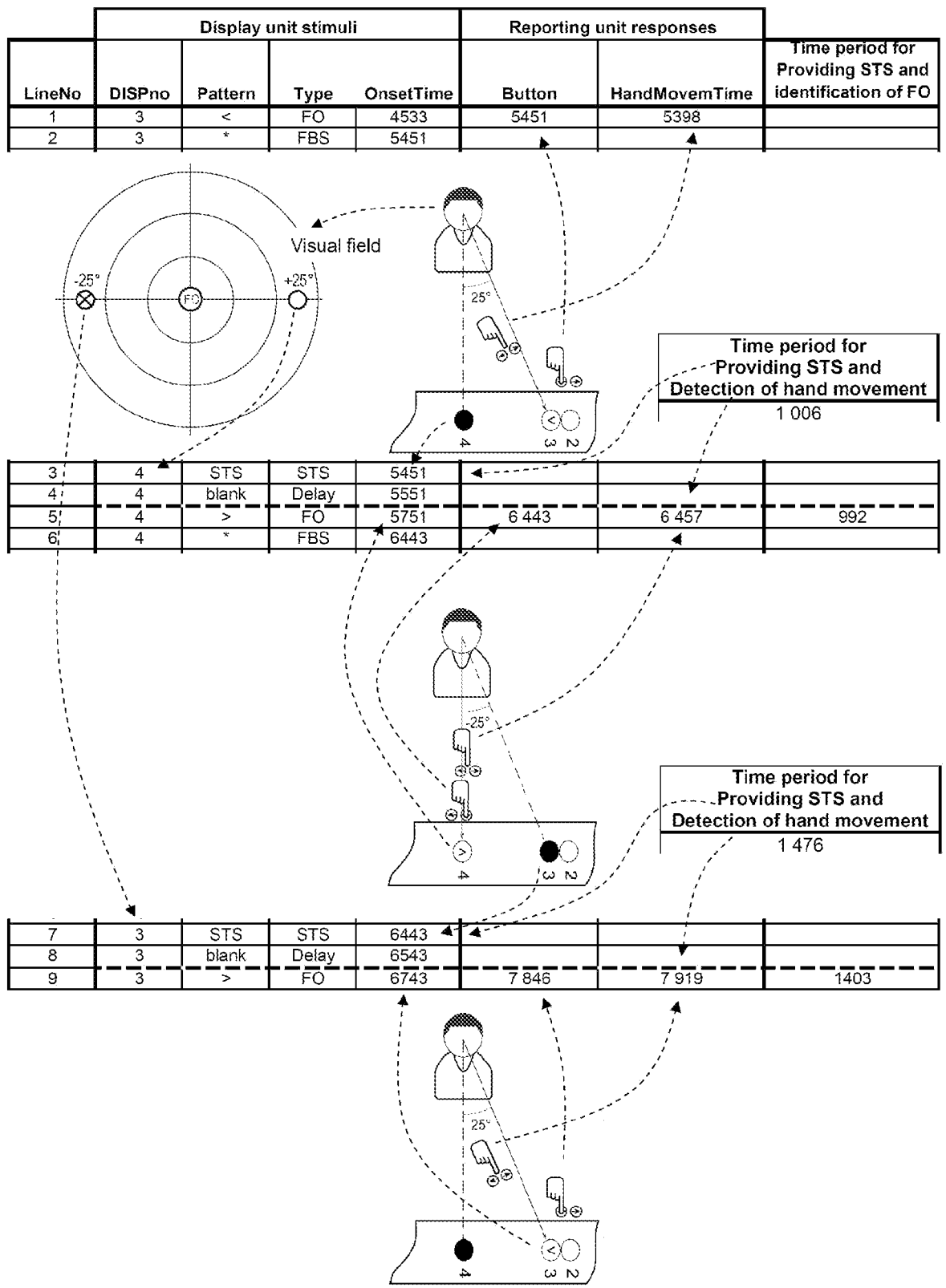
FIG. 8 illustrates a sequence of an examination where a person has a defective visual field location.

FIG. 8 illustrates a sequence of an embodiment where a person has a defective visual field location at 25° to the left from the fixation or the centre of the visual field. The time period for providing STS (LineNo 3) at visual field location 25° to the right from the fixation and identification of FO by pressing the button (LineNo 5) is 992 ms compared to 1403 ms when the STS is provided 25° to the left from the fixation (LineNo 7). This prolongation of the reaction time is an indication of decreased retinal sensitivity at this specific location which delays the saccade towards the STS.

Example 7

Defective Saccades to the Left

FIG. 9 illustrates a sequence of an embodiment of the invention where a person has a normal visual field, defective saccades to the left, but normal saccades to the right. The reaction time measured from the button press is prolonged when the STS is provided in the visual field to the left from the fixation compared to the situation where the STS is provided to the right from the fixation (1733 ms vs. 951 ms). When, however, reaction time is measured from hand movement (the task for the person was to point to the flashing light with his or her hand and report the direction of the arrow with the response buttons), there is not much difference (1048 ms vs 1030 ms). This is an indication of normal peripheral visual field at the locations specified but defective saccade to the left.

Example 8

Assessing the Duration of Gaze Shift

Figure 10:
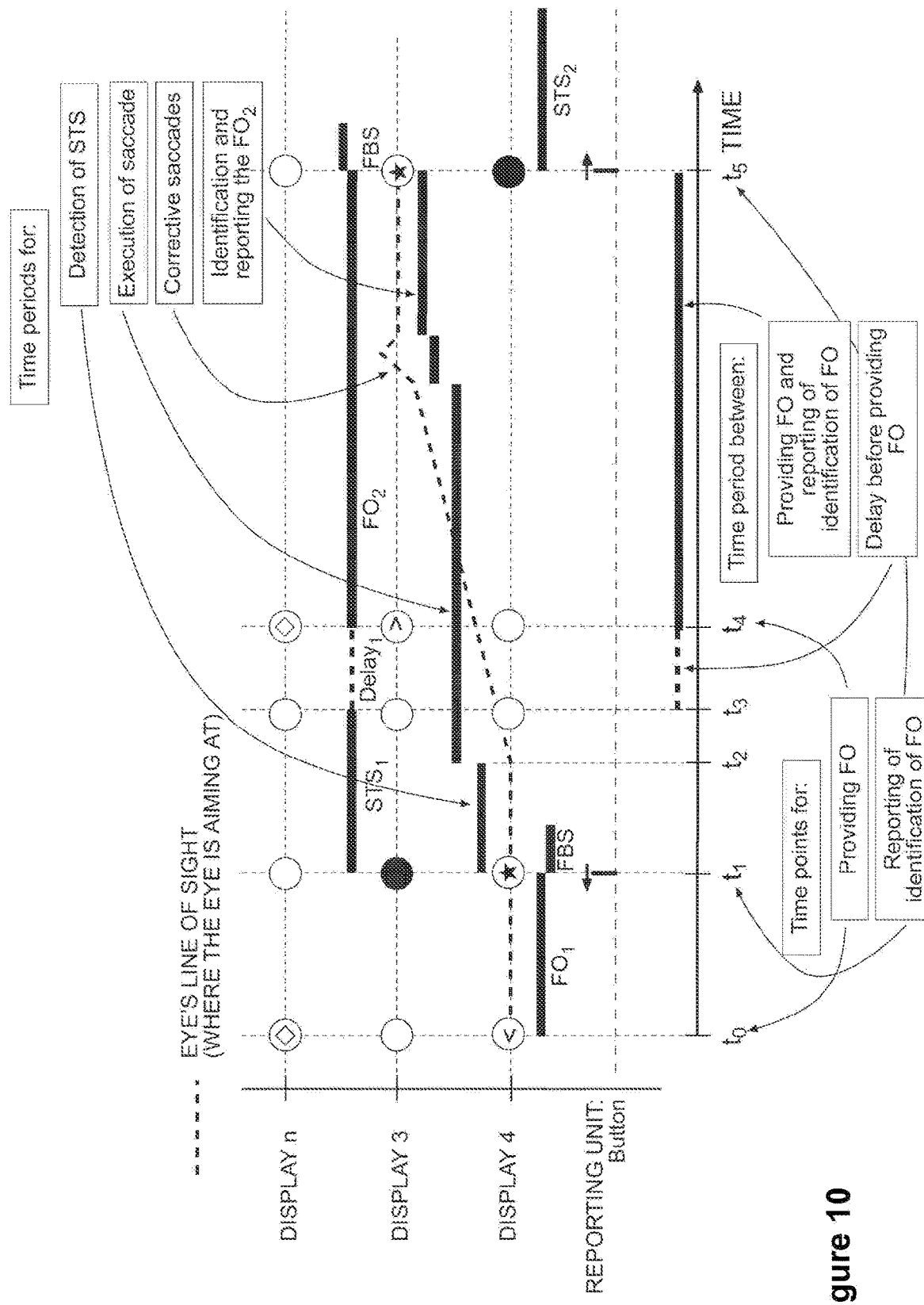
FIGS. 10 and 11 illustrate the benefit of adjusting the length of the delay before FO is provided when assessing the motor functions required of the eye and/or head to shift his or her gaze direction from one location to another.
Figure 11:
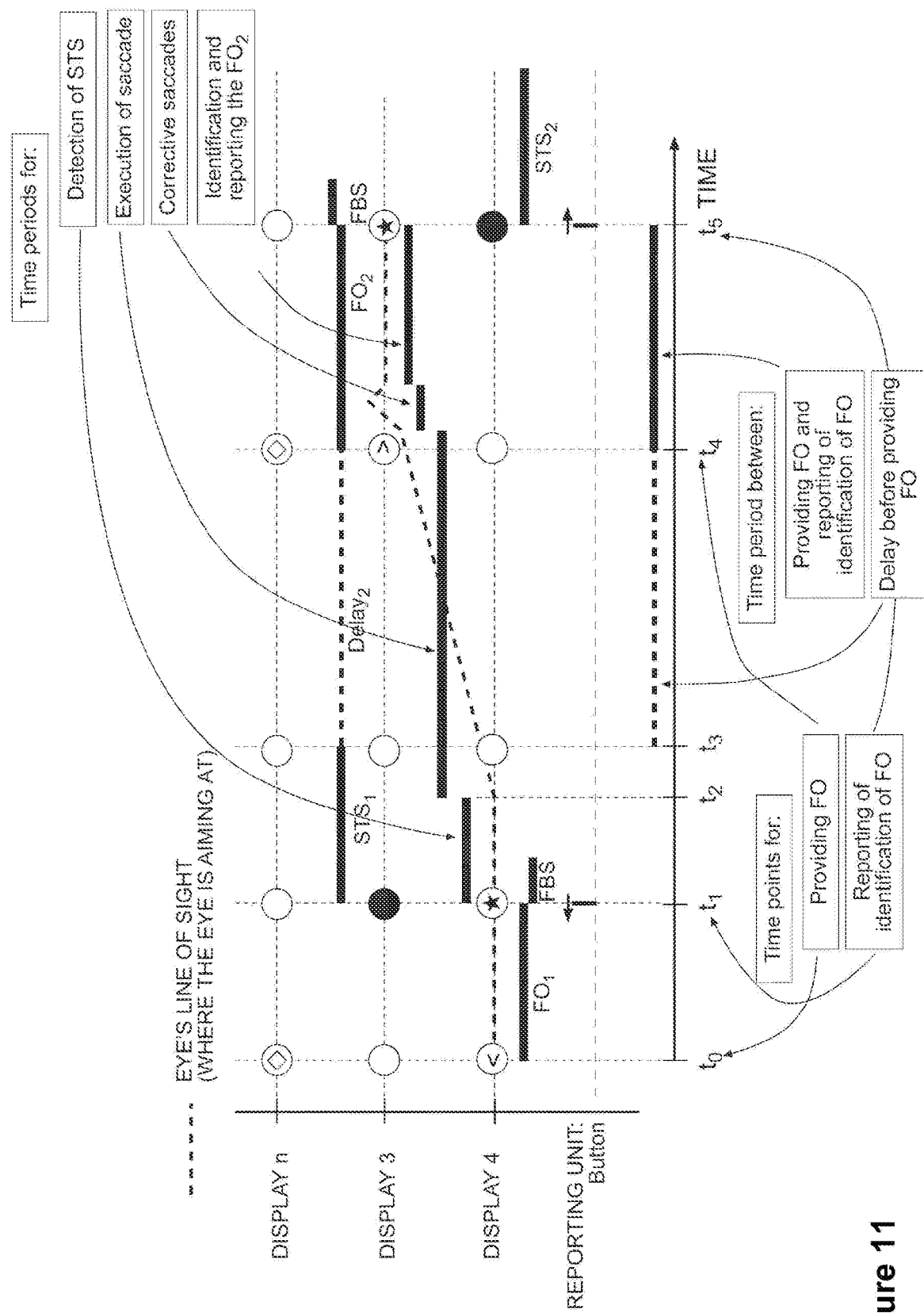

FIGS. 10 and 11 illustrate the benefit of adjusting the length of the delay, the time period between time points $t_3$ and $t_4$, before $FO_1$ is provided at location where the $STS_1$ was provided.

In FIG. 10 at time point $t_1$ the person reports the identification of $FO_1$ by pressing a correct button and thus confirming that he or she is fixating to the $FO_1$ at display unit 4. At the same time point $t_1$, at display unit 3 $STS_1$ is provided which triggers a saccade towards the location of display unit 3. The execution of the saccade and the corrective saccades in this case are so slow, that $FO_2$ at display unit 3 has been provided long before (at time point $t_4$) gaze has been directed to the location of display unit 3 for the reporting of identification of the $FO_2$ at time point $t_5$.

In FIG. 11 the same display units, and thus the same saccade length and direction, are used as in FIG. 10. Also the intensities of STS and FO stimuli are the same. In this figure longer delay ("$delay_2$") is used compared to delay in FIG. 10 ("$delay_1$") before $FO_2$ is provided at time point $t_4$ resulting shorter time period between providing FO (time point $t_4$) and reporting of identification of FO (time point $t_5$). In this way it is possible find the shortest time period between time points $t_3$ and $t_4$ which doesn't lengthen the time period between time points $t_4$ and $t_5$. In FIG. 11 the time period between $t_2$ and $t_1$ corresponds the time needed for motor functions of the eye and/or head to shift his or her gaze direction from the location of $FO_1$ (display unit 4) to STS (display unit 3).

Example 9

Assessing Function of the Visual System Employing Paragraphs of Text

Figure 12:
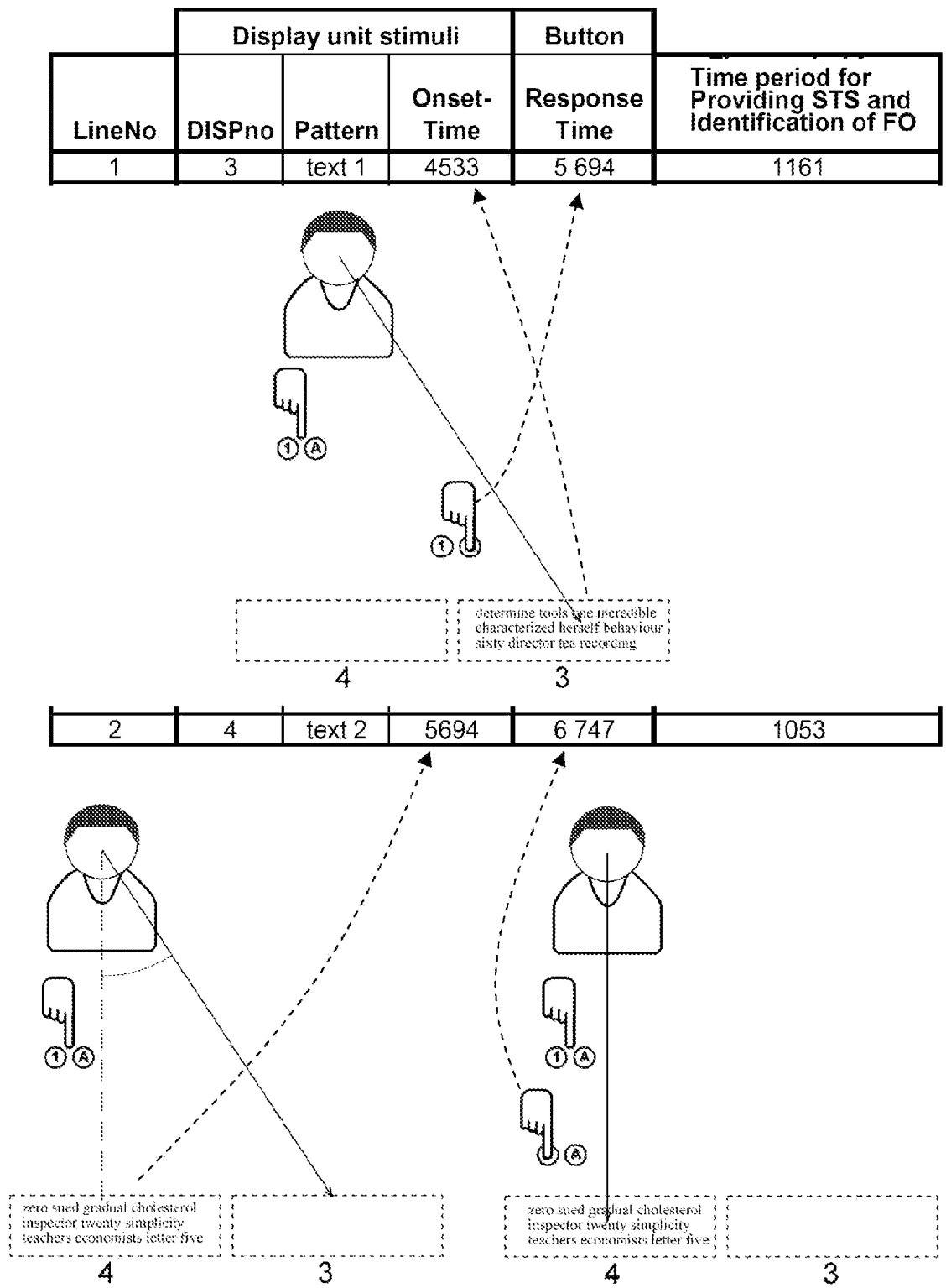
FIG. 12 illustrates assessing function of the visual system, especially reading ability, of a person employing paragraphs of text.

FIG. 12 illustrates a sequence of an embodiment of the invention assessing function of the visual system, especially reading ability, of a person with paragraphs of text. The task for a person is to read the midmost word of the paragraph, i.e. the middle word of the second line and press a button marked with '1' if the word is numeral (e.g. 'one', 'two', 'three') and a button marked with 'A' in case of other words. In FIG. 12 this midmost word of the text paragraph at display unit 3 is 'herself' and serves as a fixation object FO which the person recognizes and reports it by pressing the button marked with 'A' at time point 5694 ms (LineNo 1). At the same time at display unit 4 another text paragraph is provided (LineNo 2) which serves as peripheral saccade triggering stimulus STS. After a saccade towards the midmost word of the paragraph ('twenty') the person can report the recognition of the word by pressing the button marked with '1' at time point 6747 ms (LineNo 2). The time period for providing STS and identification of FO (the word 'twenty') is thus 6747 ms 5694 ms=1053 ms (LineNo 2).

OTHER PREFERRED EMBODIMENTS

It will be appreciated that the methods of the present invention can be incorporated in the form of a variety of embodiments, only a few of which are disclosed herein. For instance, the system can be built so that the stimuli can be displayed in two dimensions, and therefore the measurements can cover a two-dimensional visual field. Moreover the display units can be separate, unattached to each other so that they can be placed to desired locations e.g. in the examination room so that the examiner can direct the gaze of the person to desired direction when conducting e.g. fundus examination of the eye of the person. It will be apparent for the expert skilled in the field that other embodiments exist and do not depart from the spirit of the invention. Thus, the described embodiments are illustrative and should not be construed as restrictive.

The invention claimed is:

1. A system for providing markers for evaluating and/or practicing the visual field recognizable by a person's eye and/or eyes and/or visual system, said system comprising
    at least one display capable of providing at least one stimulus used in visual field examination devices, and a fixation object FO at specified locations,
    at least two sensors for monitoring ambient luminance in different areas of said display, and
    a means for adjusting a brightness of at least one of said stimulus and FO in response to monitored ambient luminance of said display in an area where the stimulus is displayed,
    wherein said means for adjusting a brightness of at least one of said stimulus and FO adjusts said brightness in different display areas of said display in response to monitored ambient luminance in said different display areas of the display.

2. The system of claim 1, wherein said stimulus is a member selected from the group consisting of a saccade triggering stimulus STS and a smooth pursuit triggering stimulus SPTS.

3. A method for evaluating and/or practicing the visual field recognizable by a person's eye and/or eyes and/or visual system, said method comprising
    providing at least one display capable of providing at least one stimulus used in visual field examination devices, and a fixation object FO at specified locations,
    providing at least two sensors for monitoring ambient luminance in different areas of said display, and
    adjusting a brightness of at least one of said stimulus and FO in different display areas of said display in response to monitored ambient luminance in said different display areas of the display.

4. The method of claim 3, wherein said stimulus is a member selected from the group consisting of a saccade triggering stimulus STS and a smooth pursuit triggering stimulus SPTS.

* * * * *